US012616843B2

(12) United States Patent
Taylor et al.

(10) Patent No.:  US 12,616,843 B2
(45) Date of Patent:      May 5, 2026

(54) TECHNIQUES FOR MANAGING INCONCLUSIVE OR DISAGREEING RESULTS IN ANALYSES OF PHYSIOLOGICAL PARAMETERS

(71) Applicant: Stryker Corporation, Portage, MI (US)

(72) Inventors: Tyson G. Taylor, Bothell, WA (US); Doan Huu Dinh, Seattle, WA (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 19/116,948

(22) PCT Filed: Sep. 28, 2023

(86) PCT No.: PCT/US2023/034057

§ 371 (c)(1),
(2) Date: Mar. 28, 2025

(87) PCT Pub. No.: WO2024/073012

PCT Pub. Date: Apr. 4, 2024

(65) Prior Publication Data

US 2025/0256114 A1      Aug. 14, 2025

Related U.S. Application Data

(60) Provisional application No. 63/412,255, filed on Sep. 30, 2022.

(51) Int. Cl.
*A61N 1/39*          (2006.01)
*A61B 5/00*          (2006.01)
(Continued)

(52) U.S. Cl.
CPC .......... *A61N 1/39044* (2017.08); *A61B 5/308* (2021.01); *A61B 5/366* (2021.01);
(Continued)

(58) Field of Classification Search
CPC .. A61N 1/39014; A61N 1/3987; A61B 5/308; A61B 5/366
(Continued)

(56) References Cited

U.S. PATENT DOCUMENTS

| 5,391,187 A | 2/1995 | Freeman |
| 9,283,400 B2 | 3/2016 | Sullivan et al. |

(Continued)

FOREIGN PATENT DOCUMENTS

WO         WO-9959673 A1 * 11/1999   ........... A61N 1/3904

OTHER PUBLICATIONS

International Search Report and Written Opinion for Application No. PCT/US2023/034057, mailed on Feb. 7, 2024, 15 pages.

*Primary Examiner* — Nadia A Mahmood
(74) *Attorney, Agent, or Firm* — Lee & Hayes, P.C.

(57)          ABSTRACT

An example method includes generating first filtered data by applying a first filter to physiological parameter data representing the physiological parameter; generating second filtered data by applying a second filter to the physiological parameter data; and determining a first index by analyzing the first filtered data. The example method further includes determining that the first index is greater than a first threshold and lower than a second threshold; and in response to determining that the first index is greater than the first threshold and lower than the second threshold, displaying the second filtered data. Upon expiration of a time period after outputting the second filtered data, the method further includes determining a second index by analyzing the first filtered data; generating a first treatment recommendation by analyzing the second index; and displaying the first treatment recommendation.

20 Claims, 9 Drawing Sheets

(51) Int. Cl.
    *A61B 5/308*         (2021.01)
    *A61B 5/366*         (2021.01)

(52) U.S. Cl.
    CPC .......... *A61B 5/4836* (2013.01); *A61B 5/7264* (2013.01); *A61N 1/3987* (2013.01); *A61N 1/3993* (2013.01)

(58) Field of Classification Search
    USPC ........................................................... 607/5
    See application file for complete search history.

(56)                References Cited

U.S. PATENT DOCUMENTS

| | | |
|---|---|---|
| 9,919,160 B2 | 3/2018 | Firoozabadi et al. |
| 10,478,630 B2 | 11/2019 | Gehman et al. |
| 10,561,853 B2 | 2/2020 | Liu et al. |
| 2016/0317073 A1 | 11/2016 | Brockway et al. |
| 2019/0329058 A1 | 10/2019 | Gehman et al. |
| 2021/0015387 A1 | 1/2021 | Sullivan et al. |
| 2022/0168583 A1* | 6/2022 | Zaidi ..................... G16H 40/63 |
| 2022/0193429 A1 | 6/2022 | Chapman et al. |
| 2023/0090464 A1 | 3/2023 | Chapman et al. |
| 2024/0052013 A1 | 2/2024 | Taylor et al. |

* cited by examiner

RESULT
203

MONITORING
DEVICE 106

ALERT
208

RECOMMENDATION
204

MODE
INDICATION
206

CHARGE
ELEMENT
216

SHOCK
ELEMENT
218

DISPLAY
SCREEN
201

SECOND FILTERED
DATA
212

RECOMMENDATION
214

MODE
INDICATION
210

DISPLAY
SCREEN
202

TREATMENT COMPONENT 110

SENSOR 108

MONITORING DEVICE 106

PARAMETER SIGNAL 302

REPORT(S) 304

INSTRUCTION(S) 306

300

400

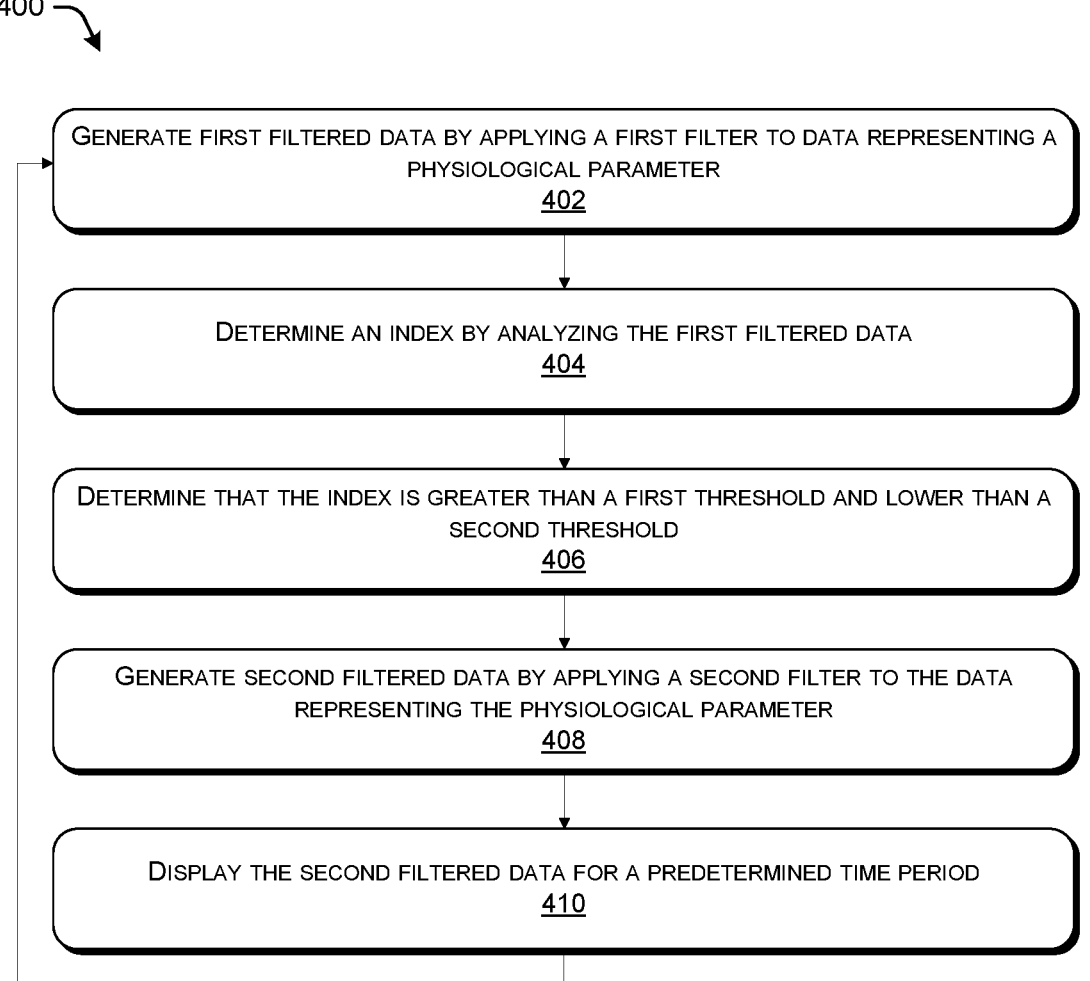

GENERATE FIRST FILTERED DATA BY APPLYING A FIRST FILTER TO DATA REPRESENTING A PHYSIOLOGICAL PARAMETER
402

DETERMINE AN INDEX BY ANALYZING THE FIRST FILTERED DATA
404

DETERMINE THAT THE INDEX IS GREATER THAN A FIRST THRESHOLD AND LOWER THAN A SECOND THRESHOLD
406

GENERATE SECOND FILTERED DATA BY APPLYING A SECOND FILTER TO THE DATA REPRESENTING THE PHYSIOLOGICAL PARAMETER
408

DISPLAY THE SECOND FILTERED DATA FOR A PREDETERMINED TIME PERIOD
410

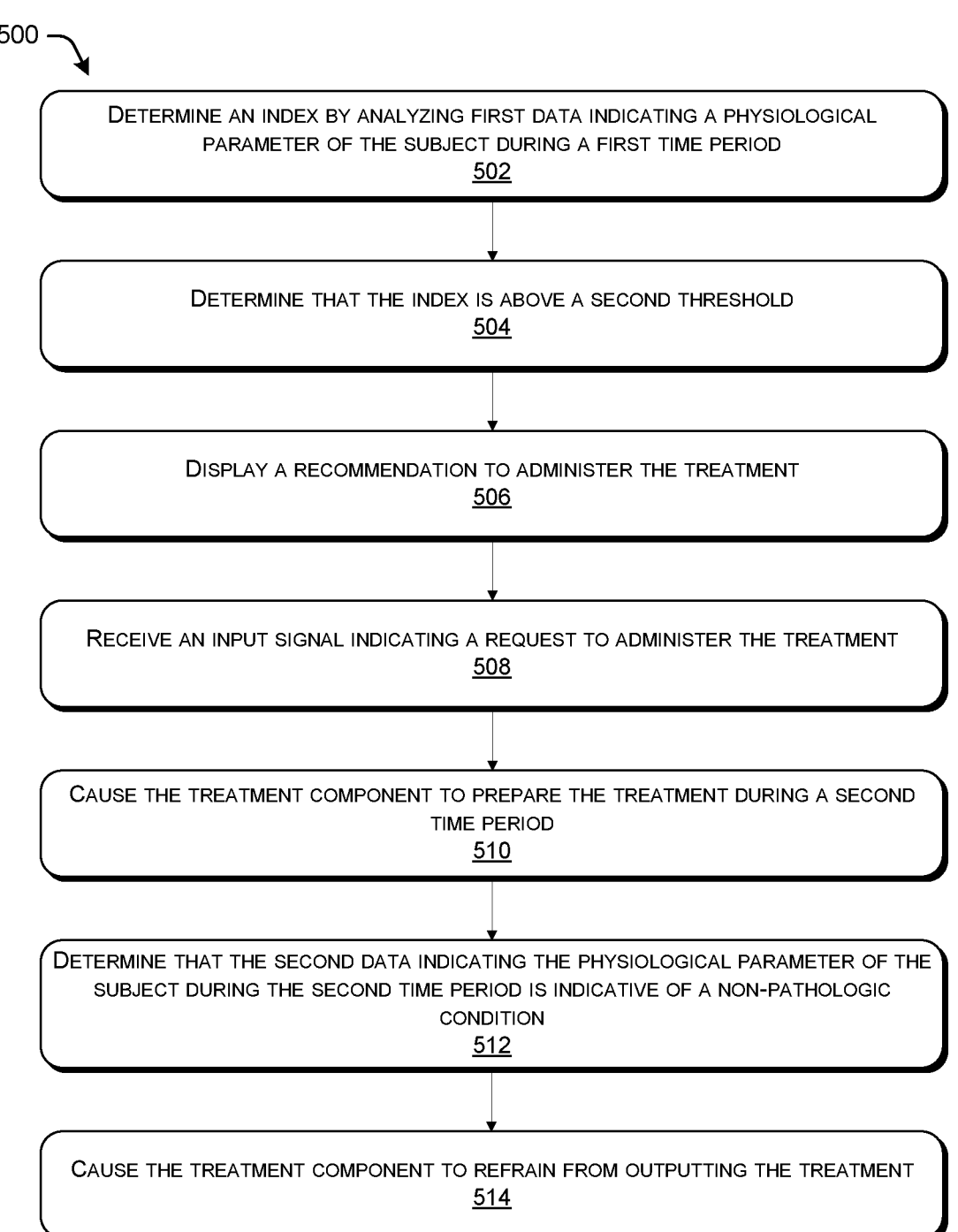

DETERMINE AN INDEX BY ANALYZING FIRST DATA INDICATING A PHYSIOLOGICAL
PARAMETER OF THE SUBJECT DURING A FIRST TIME PERIOD
502

DETERMINE THAT THE INDEX IS ABOVE A SECOND THRESHOLD
504

DISPLAY A RECOMMENDATION TO ADMINISTER THE TREATMENT
506

RECEIVE AN INPUT SIGNAL INDICATING A REQUEST TO ADMINISTER THE TREATMENT
508

CAUSE THE TREATMENT COMPONENT TO PREPARE THE TREATMENT DURING A SECOND
TIME PERIOD
510

DETERMINE THAT THE SECOND DATA INDICATING THE PHYSIOLOGICAL PARAMETER OF THE
SUBJECT DURING THE SECOND TIME PERIOD IS INDICATIVE OF A NON-PATHOLOGIC
CONDITION
512

CAUSE THE TREATMENT COMPONENT TO REFRAIN FROM OUTPUTTING THE TREATMENT
514

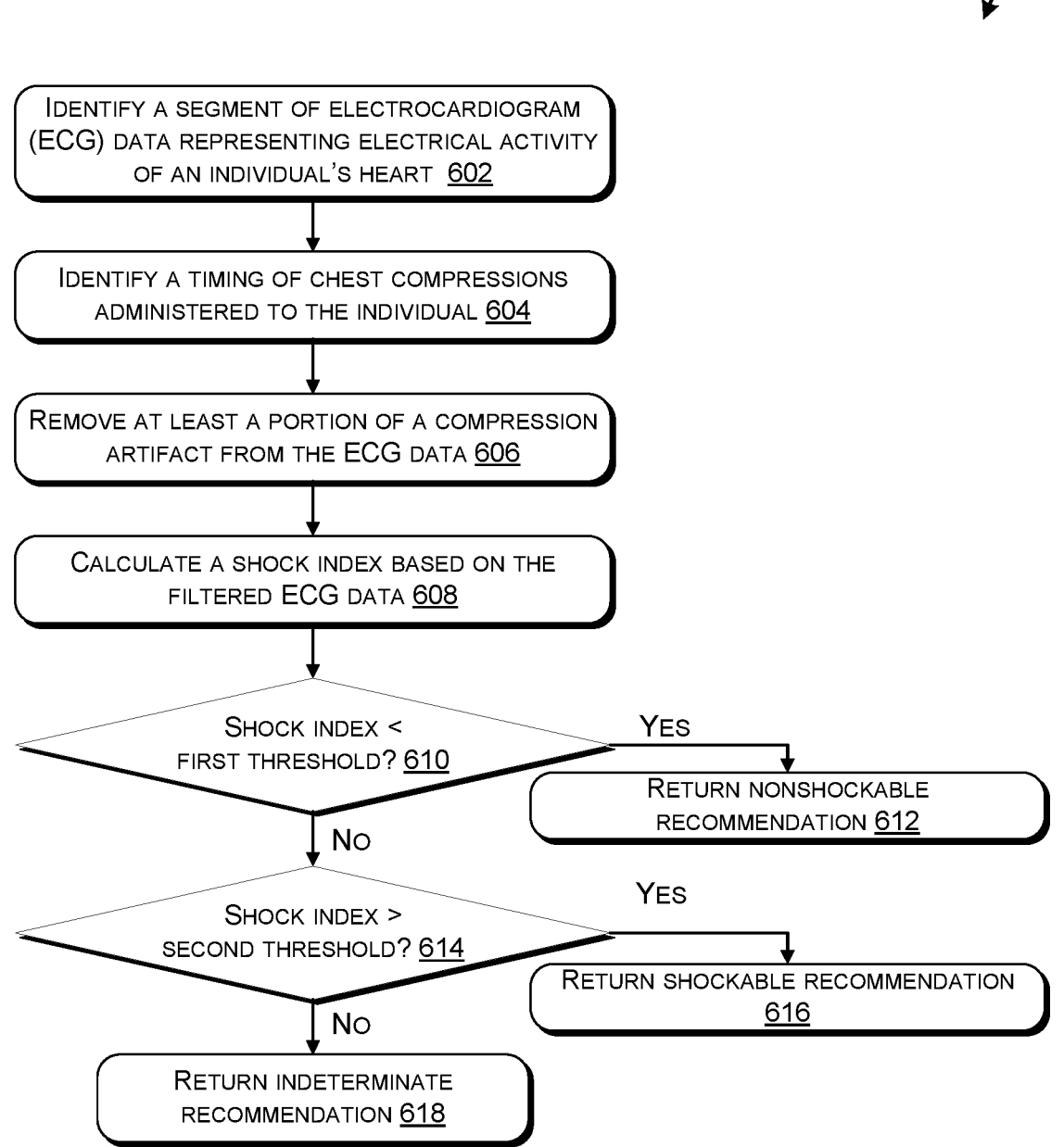

IDENTIFY A SEGMENT OF ELECTROCARDIOGRAM (ECG) DATA REPRESENTING ELECTRICAL ACTIVITY OF AN INDIVIDUAL'S HEART  602

IDENTIFY A TIMING OF CHEST COMPRESSIONS ADMINISTERED TO THE INDIVIDUAL 604

REMOVE AT LEAST A PORTION OF A COMPRESSION ARTIFACT FROM THE ECG DATA 606

CALCULATE A SHOCK INDEX BASED ON THE FILTERED ECG DATA 608

SHOCK INDEX < FIRST THRESHOLD? 610

YES

RETURN NONSHOCKABLE RECOMMENDATION 612

NO

SHOCK INDEX > SECOND THRESHOLD? 614

YES

RETURN SHOCKABLE RECOMMENDATION 616

NO

RETURN INDETERMINATE RECOMMENDATION 618

FIG. 6

TECHNIQUES FOR MANAGING INCONCLUSIVE OR DISAGREEING RESULTS IN ANALYSES OF PHYSIOLOGICAL PARAMETERS

CROSS-REFERENCE TO RELATED APPLICATIONS

This application is a U.S. National Phase Application based on International Patent Application No. PCT/US2023/034057, filed on Sep. 28, 2023, which claims the priority of U.S. Provisional App. No. 63/412,255, filed on Sep. 30, 2022, and each of which is incorporated by reference herein in its entirety.

BACKGROUND

Medical devices are configured to detect various physiological parameters. In some cases, they analyze data representing physiological parameters to determine whether a patient has a physiological condition. However, sometimes, the results of those analyses are inconclusive.

BRIEF DESCRIPTION OF THE DRAWINGS

FIG. 4 illustrates an example process for managing inconclusive results in analysis of a physiological parameter.

FIG. 5 illustrates an example process for managing treatment output based on multiple instruction inputs.

FIG. 6 illustrates an example process for identifying a shockable arrhythmia in ECG data that includes a chest compression artifact.

DETAILED DESCRIPTION

Figure 1:
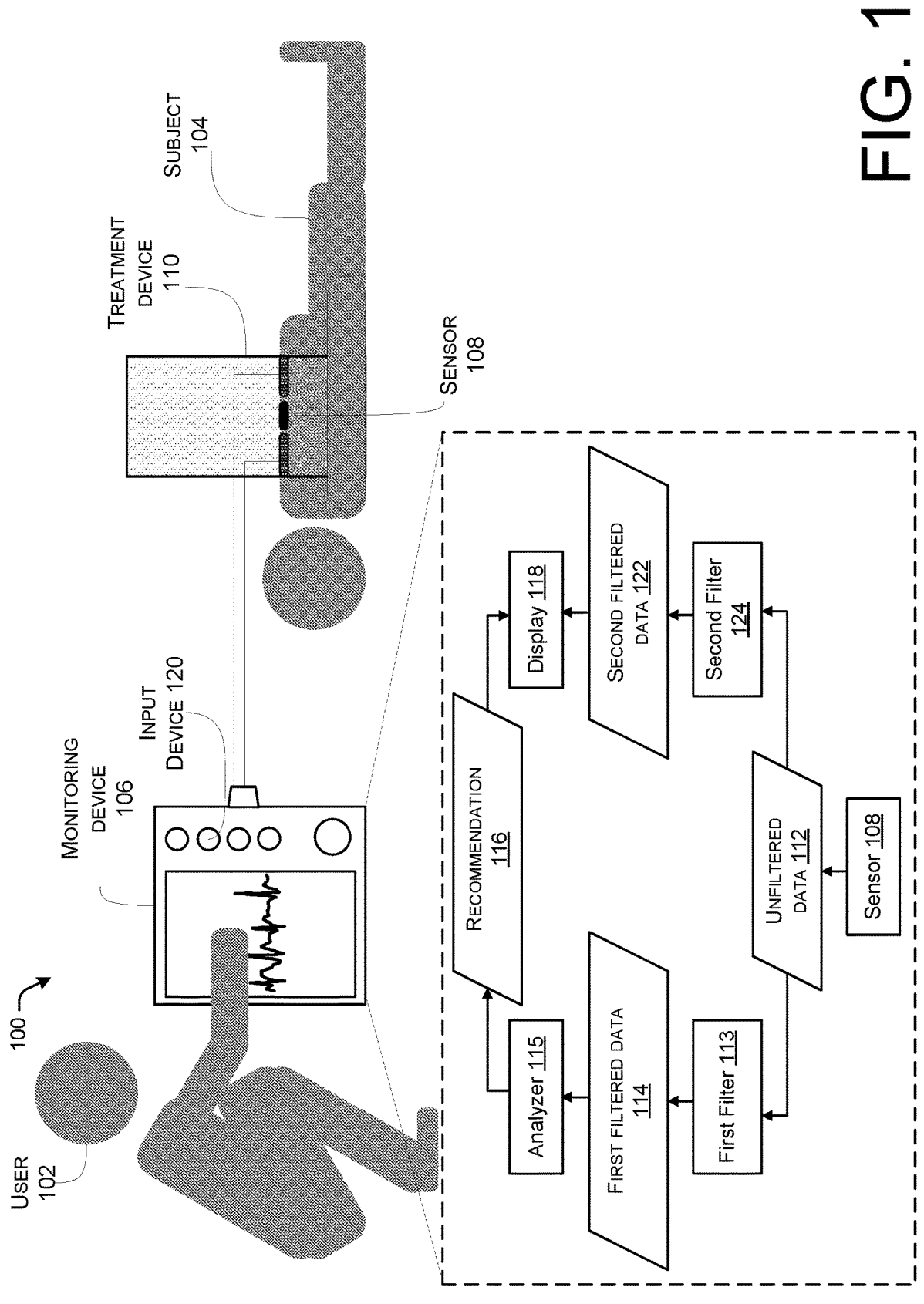
FIG. 1 illustrates an example environment for selectively outputting processed data to a user and controlling delivery of treatment based on multiple instruction inputs.

Various implementations described herein relate to managing inconclusive or disagreeing results in analysis of a physiological parameter of a subject detected by a monitoring device. In particular cases, data representing the physiological parameter includes an artifact caused by a treatment administered to the subject, such as chest compressions or cardiopulmonary resuscitation (CPR). In various cases, a monitoring device is configured to remove the artifact and/or filter the data in order to determine if the subject is in need of an additional treatment. For example, a monitor-defibrillator removes a chest compression artifact from an electrocardiogram (ECG) of a patient receiving chest compressions to determine if the subject is exhibiting a shockable arrhythmia that is treatable by an electrical shock. The term "shockable arrhythmia" refers to a rhythm treatable by defibrillation, such as ventricular fibrillation (VF) or pulseless ventricular tachycardia (VT). However, in some examples, the monitoring device is unable to determine whether the subject is in need of the additional treatment.

For instance, an analysis performed by the monitoring device produces an inconclusive result.

In some examples, the monitoring device may be able to identify whether the subject has the shockable arrhythmia in data that lacks the artifact. For instance, this problem could be addressed by pausing the ongoing treatment (e.g., CPR) and analyzing the data without the artifact present. However, pausing CPR has been shown to result in decreased chances of survival in cardiac arrest patients. Thus, it would be advantageous to accurately assess the subject's condition without pausing CPR.

Various implementations of the present disclosure address these and other problems by selectively outputting filtered physiological parameter data when the monitoring device is unable to automatically determine whether a treatment is indicated. For instance, the monitoring device generates first filtered data by removing an artifact from unfiltered physiological parameter data using a first filter (e.g., a non-comb filter). The monitoring device performs an analysis on the first filtered data to determine whether the first filter data indicates that a treatment is warranted. However, if the monitoring device is unable to conclude whether the treatment is or is not warranted, the monitoring device outputs second filtered data to the user for manual review. In various cases, the monitoring device generates the second filtered data by removing the artifact from the unfiltered physiological parameter data using a second filter (e.g., a comb filter) that is different than the first filter. The first filtered data, for instance, is suitable for analysis by the monitoring device but is unsuitable for manual review by the user. In contrast, the second filtered data may be inferior for analysis by the monitoring device but is suitable for manual review by the user. Accordingly, in examples where the monitoring device is unable to conclude whether the treatment is indicated, the monitoring device enables the user to manually assess the condition of the patient, even when the artifact is present in the unfiltered physiological parameter data. For instance, if the monitoring device is unable to determine whether an ECG of a patient receiving chest compressions is indicative of a shockable arrhythmia, the monitoring device provides the ECG without a chest compression artifact to a rescuer, thereby enabling the rescuer to manually assess the ECG without pausing the chest compressions.

In particular cases, the monitoring device determines that a first segment of an ECG of a subject receiving chest compressions includes a shockable arrhythmia and begins to charge a capacitor in accordance with a desired electrical shock dosage level by the time the CPR period has ended. But if the subject's arrhythmia resolves during this CPR period, defibrillation is no longer indicated by the time the capacitor is fully charged. In other situations, a subject may begin to experience an arrhythmia before the end of a CPR period. In various implementations of the present disclosure, the monitoring device re-evaluates the ECG of the subject during the CPR period. For instance, if the monitoring device determines that the subject's ECG indicates that the arrhythmia is resolved during the CPR period, then the monitoring device prevents the electrical shock from being administered to the subject.

Implementations of the present disclosure are directed to specific technical improvements to the field of medical devices. These technical improvements resolve inconclusive or disagreeing results of ECG analyses without requiring CPR pauses. The process overcomes the need for an emergency medical team from pausing CPR, manually reading a subject's physiological parameter, deciding whether to administer treatment, and resuming CPR. Therefore, this is a practical application in the field of medical devices.

Various examples will now be described with reference to the accompanying drawings.

FIG. 1 illustrates an example environment 100 for selectively outputting processed data to a user 102 and controlling delivery of treatment based on multiple instruction inputs. In various implementations, the environment 100 includes a rescue scene. The rescue scene, in some implementations, is in a clinical environment (e.g., a hospital) or a non-clinical environment (e.g., the scene of an accident).

In various implementations, the user 102 is treating a subject 104 at the rescue scene. For instance, the user 102 is an emergency medical technician (EMT) professional monitoring and/or treating a medical condition of the subject 104. In some cases, the subject 104 is experiencing cardiac arrest, respiratory arrest, or some other dangerous medical condition.

The user 102 monitors the condition of the subject 104 using a monitoring device 106. For instance, the monitoring device 106 may be a monitor-defibrillator, a medical imaging device, an ultrasound monitor, a standalone ECG monitor, or another type of subject monitor. The monitoring device 106 includes and/or is communicatively coupled to a sensor 108. The sensor 108 is configured to detect at least one physiological parameter of the subject 104. As used herein, the term "physiological parameter," and its equivalents, may refer to an indication of a subject's health including, for instance, an ECG, an impedance (e.g., transthoracic impedance), a force administered to the subject 104, a blood pressure, an airway parameter (e.g., a partial pressure of carbon dioxide, a partial pressure of oxygen, a capnograph, an end tidal gas parameter (e.g., end-tidal CO2 (EtCO2)), a flow rate, etc.), a blood oxygenation (e.g., a pulse oximetry value, a regional oximetry value (e.g., cerebral regional tissue oxygen saturation), etc.), an electroencephalogram (EEG), a temperature, a heart sound, a blood flow rate, a physiological geometry (e.g., a shape of a blood vessel, an inner ear shape, etc.), a heart rate, a pulse rate, a CPR position, or the like. For example, the sensor 108 includes at least one of electrodes, a detection circuit, defibrillator pads, a force sensor, a blood pressure cuff, an ultrasound-based blood pressure sensor, an invasive (e.g., intra-arterial) blood pressure sensor (e.g., including a cannula inserted into the subject 104), a gas sensor (e.g., a carbon dioxide and/or oxygen sensor), a flowmeter, a pulse oximetry sensor, a regional oximetry sensor, a thermometer, a microphone, an ultrasound transducer, a medical imaging device (e.g., an ultrasound imaging device), or the like. In various cases, the monitoring device 106 generates physiological parameter data that is indicative of one or more physiological parameters detected by the sensor 108.

A treatment device 110 (also referred to as a "treatment component") administers a treatment to the subject 104. For example, the treatment device 110 is a monitor-defibrillator, an automated external defibrillator (AED), mechanical chest compression device, a smart bag-valve mask, a ventilator, a heart-lung machine, an intravenous fluid (IV) pump, or the like. Examples of treatments include defibrillation, pacing, cardioversion, administration of chest compressions, administration of oxygen to the airway of the subject 104, movement of air in the airway of the subject 104, administration of fluids to the subject 104, extracorporeal membrane oxygenation (ECMO), administration of a medication to the subject 104, or the like. In some implementations, the monitoring device 106 is also configured to administer a treatment to the subject 104. Further, in some cases, the treatment device 110 includes one or more sensors configured to detect one or more physiological parameters of the subject 104. In particular implementations, the treatment device 110 includes two or more medical devices such as a monitor-defibrillator and a mechanical chest compression device.

In various implementations, the monitoring device 106 and the treatment device 110 are communicatively coupled to one another. In particular examples, the monitoring device 106 or the treatment device 110 reports a detected physiological parameter to the other device. For instance, the treatment device 110 may include a blood pressure sensor and may report a blood pressure of the subject 104 to the monitoring device 106. In some cases, the monitoring device 106 or the treatment device 110 reports a treatment parameter to the other device. As used herein, the term "treatment parameter," and its equivalents, refers to a characteristic of a treatment being performed on a subject 104. In some examples, the treatment device 110 reports a frequency of chest compressions administered by the treatment device 110 to the monitoring device 106. The receiving device may perform one or more actions based on the physiological parameter and/or the treatment parameter. Actions performed by the monitoring device 106 or the treatment device 110 include initiating a measurement of a physiological parameter at a particular time or frequency, outputting a signal to the user 102, outputting a signal to the subject 104, performing a treatment at a particular time or frequency, adjusting a treatment parameter of an ongoing treatment, or any combination thereof. According to some implementations, the monitoring device 106 or the treatment device 110 instructs the other device to perform one or more actions. The receiving device, in turn, performs the action(s) based on the instruction from the monitoring device 106 or the treatment device 110. For instance, the monitoring device 106 instructs the treatment device 110 to cease administering chest compressions to the subject 104 at a predetermined time, and the monitoring device 106 administers a defibrillation shock to the subject 104 at the particular time. By exchanging reports, instructions, or other data, the monitoring device 106 and the treatment device 110 can coordinate monitoring and treatment of the subject 104.

To exchange data, the monitoring device 106 and/or the treatment device 110 are configured to establish and/or communicate via a communication channel. As used herein, the term "communication channel," and its equivalents, may refer to a medium over which a first endpoint (e.g., a sender) transmits information to one or more second endpoints (e.g., receivers). Examples of communication channels include wired connections, such as Ethernet or fiber optic paths, as well as wireless connections, such as Institute of Electronics and Electrical Engineers (IEEE) (e.g., WI-FI, BLUETOOTH, etc.) or 3$^{rd}$ Generation Partnership Program (3GPP) (e.g., Long Term Evolution (LTE), New Radio (NR), etc.) connections. As used herein, the term "endpoint," and its equivalents, may refer to an entity that is configured to transmit and/or receive data. Examples of endpoints include user equipment (UE) (e.g., mobile phones, tablet computers, etc.), computers, base stations, access points (APs), servers, compute nodes, medical devices, Internet of Things (IoT) devices, and the like.

In some implementations, the communication channel between the monitoring device 106 and the treatment device 110 is established when the monitoring device 106 and the treatment device 110 are paired. In particular cases, the monitoring device 106 and treatment device 110 refrain from sharing substantive data (e.g., physiological parameters or other metrics, reports about the subject 104, instructions for treating the subject 104, etc.) until the monitoring device 106 and the treatment device 110 are paired. As used herein, the term "paired," and its equivalents, may refer to a state of multiple devices that have a shared link key that enables each device to cryptographically authenticate data it receives from any other device among the multiple devices. In some cases, paired devices communicate wirelessly.

In particular cases, a first paired device encrypts data prior to transmitting the data to a second paired device, and the second paired device restores the original data by decrypting the encrypted data. As used herein, the term "encrypt," and its equivalents, refers to a process of translating data from one format (e.g., an unencoded format) into an encoded format. In various cases, the encoded format is referred to as "ciphertext." Unencoded data, which has not been encrypted, may be referred to as being in "plaintext." In various examples, an entity encrypts data using at least one encryption key. An encryption key is a parameter that defines the translation of data from the one format into the encoded format. As used herein, the term "decrypt," and its equivalents, refers to a process of translating data from an encoded format into another format (e.g., an unencoded format), such as a plaintext format. In various examples, an entity encrypts data using at least one decryption key. A decryption key is a parameter that defines the translation of data from the encoded format into the other format. A link key, for example, is an encryption and/or decryption key.

Various cryptographic techniques can be utilized in accordance with the features described in this disclosure. For example, data can be encrypted and decrypted via a symmetric key, wherein the encryption key and the decryption key are equivalent. In some cases, data can be encrypted and decrypted via asymmetric keys, wherein the encryption key and the decryption key are different. Cryptographic hash functions (CHFs) are examples of cryptographic techniques. Examples of cryptographic techniques include the Data Encryption Standard (DES), Advanced Encryption Standard (AES), Elliptic Curve Cryptography (ECC), Rivest-Shamir-Adleman (RSA), Secure Hash Algorithm (SHA)-1, SHA-2, SHA-3, BLAKE, BLAKE2, BLAKE3, WHIRLPOOL, MD2, MD4, MD5, MD6, Temporal Key Integrity Protocol (TKIP), Rivest cipher 4 (RC4), variably modified permutation composition (VMPC), blowfish, Twofish, Threefish, Tiny Encryption Algorithm (TEA), Extended TEA (XTEA), Corrected Block TEA (XXTEA), Diffie-Hellman exchange (DHE), elliptic curve DHE, supersingular isogeny Diffie-Hellman (SIDH) key exchange, and so on. Any suitable encryption or decryption technique can be used in accordance with implementations of this disclosure.

In various implementations of the present disclosure, the monitoring device 106 generates unfiltered data 112 based on the physiological parameter detected by the sensor 108. For example, the monitoring device 106 includes an analog-to-digital converter (ADC) that converts a signal representing the physiological parameter into digital data. However, in particular implementations, the subject 104 is simultaneously receiving the treatment from the treatment device 110. In various cases, the treatment generates an artifact in the unfiltered data 112. For instance, the unfiltered data 112 represents an ECG of the subject 104 while the subject 104 is receiving chest compressions from the treatment device 110, such that the unfiltered data 112 includes a chest compression artifact.

The artifact in the unfiltered data 112 may impede review of the physiological parameter by the user 102 and/or the monitoring device 106. In some cases, the user 102 is unable to identify whether the subject 104 is experiencing a dangerous medical condition due to the presence of the artifact. For example, the user 102 may be unable to determine whether the subject 104 is experiencing an arrhythmia treatable by defibrillation due to the presence of the chest compression artifact in the unfiltered data 112 representing the ECG of the subject 104. While the user 102 could temporarily pause the chest compressions by operating the treatment device 110 and view the unfiltered data 112 without the chest compression artifact, such a pause in chest compressions could harm the subject 104. Thus, in some implementations, it is preferred to avoid pauses in chest compressions and other treatments during rescue events.

In various implementations of the present disclosure, the monitoring device 106 is configured to generate first filtered data 114 by at least partially removing the artifact from the unfiltered data 112 using a first filter 113. For example, the monitoring device 106 generates the first filtered data 114 representing an ECG segment by removing at least a portion of the chest compression artifact from the unfiltered data 112. The segment has a time period that is greater than or equal to 3 seconds and less than or equal to 30 seconds, for instance. In some examples, the monitoring device 106 generates the first filtered data 114 representing the ECG by removing at least a portion of the chest compression artifact from samples of the unfiltered data 112, wherein the samples are separated in the time domain by a time interval that is greater than the sampling period of the unfiltered data 112. In various examples, the monitoring device 106 removes at least the portion of the chest compression artifact by applying an adaptive filter (e.g., a Wiener filter, a Kalman filter, or the like), applying an inverse comb filter, applying a high-pass filter, applying a band reject filter, applying a finite impulse response (FIR) filter, applying an infinite impulse response (IIR) filter, identifying and subtracting the chest compression artifact, or a combination thereof. In various cases, the first filter 113 omits a comb filter. In some cases, the monitoring device 106 converts the unfiltered data 112 and/or first filtered data 114 from the time domain into the frequency (e.g., a Fourier) domain, a Laplace domain, a Z-transform domain, or a wavelet (e.g., a continuous wavelet transform, a discrete wavelet transform, etc.) domain, and removes the chest compression artifact by analyzing the converted unfiltered data 112 and/or first filtered data 114. Although this disclosure specifically describes various techniques for generating the first filtered data 114 representing an ECG segment, other techniques known in the art of signal processing can be used to generate the first filtered data 114.

In particular implementations, the monitoring device 106 generates a shock index based on the first filtered data 114. For example, the first filtered data 114 may be in a format that is suited for an automated, computer-based analysis of the physiological parameter of the subject 104. However, the first filtered data 114 may include characteristics that make it unsuitable for manual review by the user 102. In various examples, the shock index corresponds to a likelihood and/or certainty that the first filtered data 114 is indicative of a shockable arrhythmia and/or that the subject 104 exhibits the shockable arrhythmia during the time period corresponding to the segment of the first filtered data 114. In some cases, the monitoring device 106 determines whether the shockable arrhythmia is present in the first filtered data 114 by comparing the shock index to at least one threshold. In some implementations, the analyzer 115 determines a recommendation 116 based on the shock index. For example, the analyzer 115 determines that the filtered data is indicative of a shockable arrhythmia if the shock index is lower than a first threshold and greater than a second threshold, that the first filtered data 114 is indicative of a nonshockable rhythm (i.e., the shockable arrhythmia is absent) if the shock index is less than a first and greater than a second threshold, and that it is unclear whether the first filtered data 114 is indicative of a shockable arrhythmia (e.g., an "indeterminate" decision or "inconclusive" decision) if the shock index is greater than the first threshold and less than the second threshold. In alternate examples, the monitoring device 106 determines that the first filtered data 114 is indicative of the shockable arrhythmia if the shock index is less than the first and second thresholds and determines that the first filtered data 114 is indicative of the nonshockable rhythm if the shock index is greater than the first and second thresholds.

Although FIG. 1 is described with reference to "shock indices," which correspond to whether a heart rhythm is treatable by defibrillation, implementations are not so limited. For example, other types of indices corresponding to other types of treatments can be calculated based on other types of physiological parameters. In various implementations, the monitoring device 106 calculates a treatment index based on the first filtered data 114, where the treatment index corresponds to a likelihood that the first filtered data 114 is indicative of a condition that can be addressed by a treatment. The monitoring device 106 may conclude that the subject 104 has the treatable condition, does not have the treatable condition, or that the monitoring device 106 is unable to conclude whether the subject 104 has the treatable condition by comparing the index to one or more thresholds.

In particular implementations, the monitoring device 106 includes a display 118 and/or one or more output devices that outputs information to the user 102. For example, the display 118 visually presents the recommendation 116 based on the index. According to some cases, the recommendation 116 indicates that the subject 104 has the treatable condition (e.g., "shock"), that the subject 104 does not have the treatable condition (e.g., "no shock"), or that the monitoring device 106 is unable to conclude whether the subject 104 has the treatable condition (e.g., "inconclusive") based on the analysis of the first filtered data 114. If the recommendation 116 indicates that the subject 104 has a shockable arrhythmia, then the user 102 may instruct the monitoring device 106 to prepare the treatment by indicating this action via an input device 120. For example, the monitoring device 106 may begin to charge a capacitor that, when discharged, would administer an electrical shock to the subject 104.

Preparing the treatment, however, may take a particular time period. For instance, it may take seconds or even minutes to sufficiently charge a capacitor to administer an electrical shock at a particular dosage to the user 102. During this time period, the condition of the user 102 may change. In various implementations, the user 102 may exhibit a non-pathologic condition during the treatment preparation period. As used herein, the term "non-pathologic condition" may refer to a condition that is not improved by a treatment, or for which the treatment is not indicated. For example, the first filtered data 114 may indicate that the user 102 has developed an organized rhythm including multiple QRS complexes during the charging period of the capacitor.

In various implementations of the present disclosure, the monitoring device 106 may re-evaluate the first filtered data 114 while the treatment is being prepared. In some cases, the monitoring device 106 alters the recommendation 116 based on the re-evaluated first filtered data 114. For example, if the recommendation 116 changes to indicate that the treatment not be administered to the subject 104, then the monitoring device 106 may cancel the treatment. In some cases in which the monitoring device 106 is charging a capacitor, the monitoring device 106 discharges the capacitor to ground without administering an electrical shock to the subject 104.

In some cases, the monitoring device 106 is unable to conclude whether the subject 104 has the treatable condition using the first filtered data 114. For example, the monitoring device 106 determines that an index (e.g., shock index) is between a first threshold and a second threshold.

According to various implementations of the present disclosure, the monitoring device 106 outputs second filtered data 122 to the user 102 in response to being unable to determine whether the subject 104 has the treatable condition using the first filtered data 114. In particular implementations, the monitoring device 106 generates second filtered data 122 by removing the artifact from the unfiltered data 112 using a second filter 124. The second filter 124 is and/or includes a different type of filter than the first filter 113. For instance, the second filter 124 includes a comb filter and/or one or more notch filters. For instance, the second filter 124 could be a comb filter and the first filter 113 could include an adaptive filter, an inverse comb filter, a high-pass filter, a band reject filter, a FIR filter, or an IIR filter.

In particular cases, the monitoring device 106 generates the second filtered data 122 by applying a comb filter or multiple notch filters to the unfiltered data 112. For instance, comb filters are particularly suited to remove chest compression artifacts administered by a mechanical chest compression device. In some cases, an example comb filter rejects a band including the frequency of the chest compressions as well as one or more harmonics of the frequency. In some implementations, the treatment device 110 reports the frequency of the chest compressions and/or reports the start and stop of the chest compressions to the monitoring device 106 over the communication channel, and the monitoring device 106 generates and/or adjusts the filter applied to the unfiltered data 112 accordingly. In some implementations, the monitoring device 106 identifies the frequency of the chest compressions by analyzing the unfiltered data 112 itself.

In various cases, the presence of the treatable condition is easier to manually discern in the second filtered data 122 than the first filtered data 114. For example, the first filter 113 may introduce additional artifacts and/or distortion into the first filtered data 114 that is absent from the second filtered data 122. Accordingly, the first filtered data 114 may be optimized for computer-based analysis, but the second filtered data 122 may be superior for manual analysis.

Thus, by outputting the second filtered data 122 to the user 102, the monitoring device 106 may enable the user 102 to manually determine whether the subject 104 has the treatable condition even when the monitoring device 106 is unable to discern, for itself, whether the subject 104 has the treatable condition. This additional, conditional level of manual review increases the likelihood that the user 102 will correctly diagnose the condition of the subject 104. In addition, because the artifact is removed from the second filtered data 122, the user 102 may be able to accurately identify whether the treatable condition is present without pausing the ongoing treatment (e.g., chest compressions) administered to the subject 104.

In particular implementations, after reviewing the second filtered data, the user 102 can provide an input signal via the input device 120 at any time in the resuscitation indicating the presence of a shockable rhythm (e.g., VF) and the treatment (e.g., electrical shock) is coordinated and delivered by the treatment device 110 at a pre-designated time. For example, the user 102 may indicate a shockable rhythm (e.g., VF) via the input device 120 and the monitoring device 106 automatically coordinates the delivery of the treatment (e.g., electrical shock) by the treatment device 110 at the pre-designated end of the CPR period. In some implementations, the input signal causes the delivery of treatment. In other implementations, the input signal coordinates the charging of the treatment device 110. In some cases, the user 102 is alerted that the treatment device 110 is charging. In In another implementation the monitoring device 106 communicates with a chest compression device to pause chest compressions and deliver the electrical shock or the monitoring device 106 coordinates delivery of the electrical shock to occur at a targeted time point in a compression-decompression cycle. In one case, the user 102 may be required to confirm instructions provided through the input device 120 to deliver and coordinate treatment. In some cases, the monitoring device 106 alerts the user 102 that treatment will be delivered. In some cases, the monitoring device 106 delivers and coordinates treatment without confirmation from the user 102.

In some cases, the second filtered data 122 is only output when the monitoring device 106 is unable to conclude whether the subject 104 has the treatable condition. In other circumstances, for instance, the second filtered data 122 is generated in the background and hidden from the user 102. By hiding the second filtered data 122 until the second filtered data 122 is needed to confirm whether the subject 104 has the treatable condition, the monitoring device 106 may reduce distractions to the user 102 at the rescue scene.

In some instances, the monitoring device 106 determines which filter to apply to the unfiltered data 112 or what to display on the display 118 based on a selected mode of analysis. For instance, the monitoring device 106 receives an input signal, from the user 102, selecting a mode of analysis. The mode of analysis, for instance, can include the type of filtered data presented on the display 118, whether an indication of the index is output on the display 118, what thresholds are being applied to the index in order to generate the recommendation 116, or any combination thereof.

In particular implementations, the monitoring device 106 can cycle through determining a shock index and providing a recommendation 116 for different time periods until the discharge circuit outputs the treatment to the subject 104. In particular implementations, the monitoring device 106 can cycle through determining a shock index and providing a recommendation 116. In another particular implementation, the monitoring device 106 can perform parallel computations to determine the shock index with each parallel computation being started at various offsets in time thereby enabling shock indices and recommendations to be provided at any chosen interval such as every 1 second, every 5 seconds, etc. or providing an apparently continuous assessment of the condition of subject 104.

Although the monitoring device 106 is illustrated in FIG. 1 as a monitor-defibrillator, implementations are not so limited. For instance, the monitoring device 106 may be a mechanical chest compression device, an imaging device, or any other device configured to detect a parameter of the subject 104. In addition, the treatment device 110 could be a monitor-defibrillator, a mechanical chest compression device, or any other device configured to administer a treatment (e.g., an electrical shock, pacing, chest compressions, etc.) to the subject 104.

In FIG. 1, the monitoring device 106 and treatment device 110 are illustrated as communicating directly. However, implementations are not so limited. For example, any illustrated and/or described communication between the monitoring device 106 and the treatment device 110 can be relayed by at least one intermediary device.

Figure 2A:
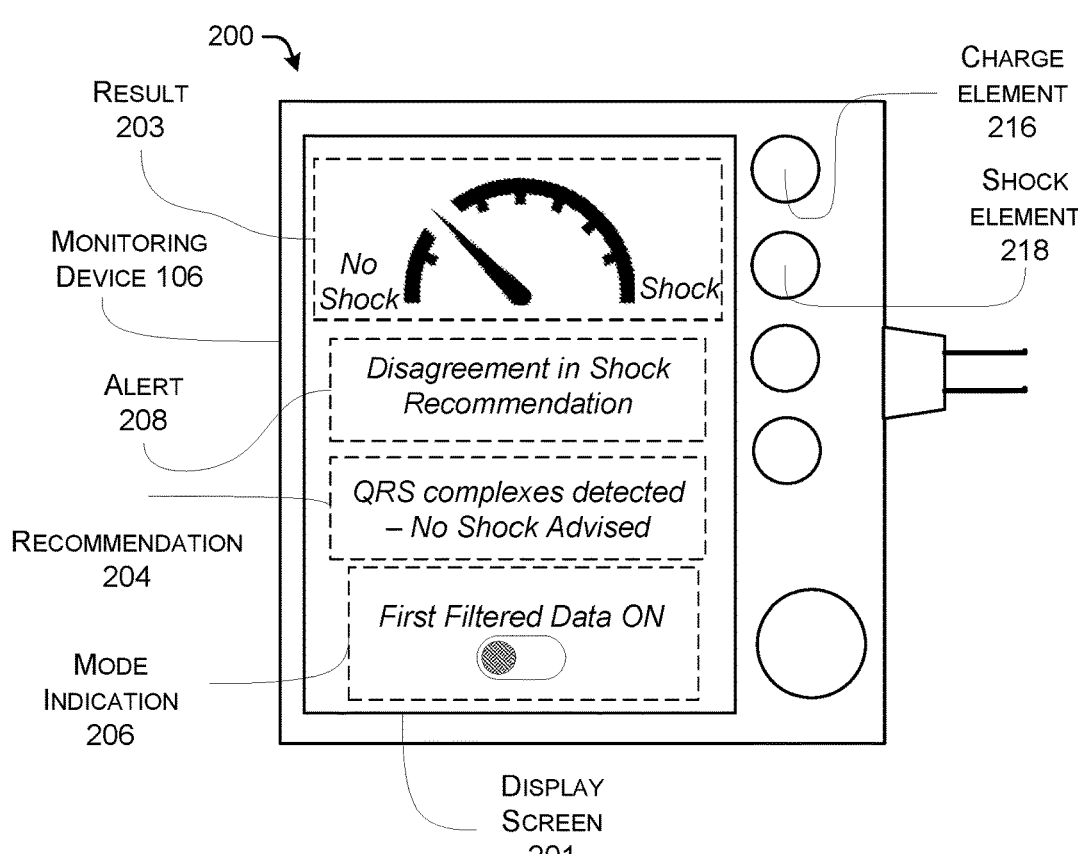
FIGS. 2A and 2B illustrate an example defibrillator with display screens that are visually presented at different times.
Figure 2B:
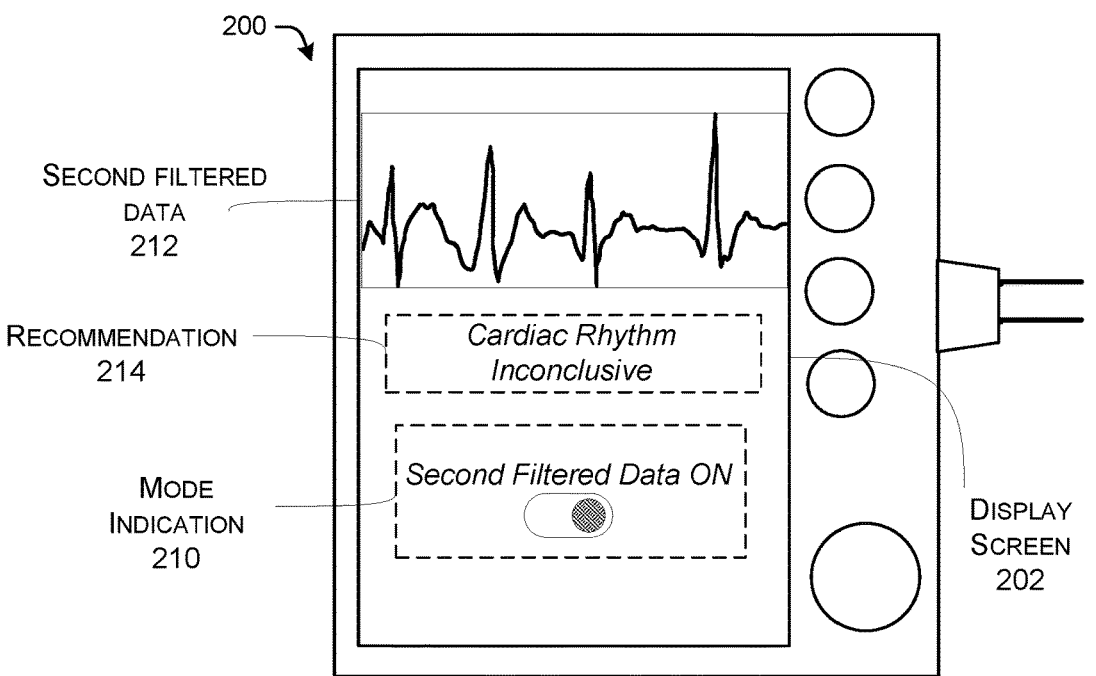

FIGS. 2A and 2B illustrate an example defibrillator 200 with example display screens 201 and 202 that are visually output at different times. FIG. 2A illustrates an example display screen 201 at a first time. FIG. 2B illustrates an example display screen 202 at a second time. The defibrillator 200 is, for example, the monitoring device 106 described above with reference to FIG. 1. In the example of FIGS. 2A and 2B, the defibrillator 200 is operating in manual mode and advisory mode. The defibrillator 200 displays the ECG-related data on display screens 201 and 202. In some examples, the display screens 201 and 202 are visually presented on a touchscreen of the defibrillator 200.

In particular implementations, the display screen 201 displays a result 203, a recommendation 204, and/or a mode indication 206. In some implementations, the result 203 includes some indication or outcome of filtering the data. The recommendation 204 illustrates the outcomes of analysis by the defibrillator 200 of the filtered data. In particular implementations, the recommendation 204 includes a shock advised, no shock advised, or inconclusive recommendation.

As shown in FIG. 2A, the defibrillator 200 applied a first filter to the unfiltered data and analyzes the filtered data to determine if the filtered data is indicative of a discernable shockable arrhythmia. In some cases, the unfiltered data includes an ECG obtained from a subject. In some cases, the defibrillator 200 selects a segment of the ECG and removes the chest compression artifact from the selected segment using one or more filtering techniques. In some examples, the defibrillator 200 generates a shock index based on the filtered ECG and determines whether the shockable arrhythmia is present by comparing the shock index to one or more thresholds. An example result of filtering the data is shown as the result 203. In further implementations, the defibrillator 200 outputs a recommendation 204 on the display screen 201 based on the analysis of the ECG. In the example illustrated in FIG. 2A, the user has already indicated a shockable arrhythmia based on analysis of the ECG during a first time period. An analysis of a segment of the ECG over a second time period by the defibrillator 200 determined that the ECG exhibits a non-shockable rhythm. The disagreement in the recommendation 204 from the first time period to the second time period is illustrated by an alert 208. In this case, the alert 208 includes a visual alert displayed on the display screen 201 but the alert 208 can also be an aural alert or a haptic alert output by the defibrillator 200. The alert 208 can include any means to notify the user of a disagreement such as text, a light indication, an alarm, a voice, or a buzz. In the example illustrated in FIG. 2A, the defibrillator 200 further determined that a non-pathologic condition (e.g., QRS complexes) was detected and thereby provided a "No Shock Advised" recommendation 204 to the display. The defibrillator 200 determined whether a non-pathologic condition was present because of the disagreement in recommendations from the first time period to the second time period. In particular implementations, the defibrillator 200 can detect a non-pathologic condition and provide a "No Shock Advised" recommendation 204 to the display without applying a first filter or determining a shock index.

In the example of FIGS. 2A and 2B, the display screens 201 and 202 also present the mode indications 206 and 210. The mode indications 206 and 210 indicate what kind of filter or algorithms are active and/or displayed. In some examples, the mode indication 206 and 210 is selectable, such that a user can activate and/or deactivate the advisory mode by entering a user input signal associated with the mode indications 206 and 210 into the defibrillator 200. For instance, the display screens 201 and 202 is a touch screen and the defibrillator 200 activates, deactivates, and/or switches the advisory mode and/or display based on a touch signal received by one or more touch sensors corresponding to the area of the mode indication 206 displayed on the display screens 201 and 202.

As shown in FIG. 2B, the defibrillator 200 includes a display screen 202 that presents a second filtered data 212. In various implementations, the display screen 202 presents the second filtered data 212, a recommendation 214, and the mode indication 210. In some cases, an ECG (filtered or unfiltered) is obtained as chest compressions are administered to the subject. An example of a filtered ECG is shown as the second filtered data 212. In some implementations, the second filtered data 212 is generated by applying a comb filter, for example, to the unfiltered data. In particular implementation, the recommendation 214 includes a shock advised, no shock advised, or inconclusive recommendation. The example as shown in FIG. 2B uses a second filter as indicated by the mode indication 210 and returns an inconclusive recommendation.

In another implementation, the display screen 202 presents the second filtered data 122 to the user regardless of a shock index. Since the second filtered data 122 can be available to the user continuously, the recommendation 214 and may differ from the user 102 assessment of the condition of subject 104. Under such conditions, the defibrillator 200 includes an input device 120 as described above in FIG. 1 further configured to enable the user 102 to indicate a disagreement with the recommendation 214. When the user 102 indicates the disagreement on the defibrillator 200, an outcome is elicited. In an example outcome, the defibrillator 200 proceeds with the instruction provided by the user 102 via the input device 120. In another example, the defibrillator 200 applies a first filter and determines a shock index. The defibrillator 200 then proceeds with providing a treatment or not providing a treatment based on the shock index. In still other examples, the defibrillator 200 can provide a prompt requesting that the user 102 confirm instructions via the input device 120.

Although not illustrated, in some cases, the defibrillator 200 is configured to output the ECG with multiple waveforms corresponding to various leads. For instance, the ECG includes twelve waveforms, arranged in rows and/or columns, corresponding to a 12-lead signal. In various examples, the 12-lead ECG is obtained from the patient during a time interval when the patient is not receiving chest compressions. The 12-lead signal, for example, assists a user with diagnosing a condition of the patient, such as ST-Elevation Myocardial Infarction (STEMI).

In further implementations, the defibrillator 200 also outputs an indication of the accuracy on the display screens 201 and 202. The accuracy indicates the certainty of the recommendation 204 and 214. In some cases, the accuracy is represented as a gauge indicating the certainty, a number, a color indicating the certainty (e.g., green for greater than 70% certainty, red for less than 70% certainty, etc.), or any other graphical user interface element that shows a readily discernible certainty to the user of the defibrillator 200.

The defibrillator 200, in some cases, charges one or more capacitors in response to an input device 120 as shown in FIG. 1 and/or the determination that the shock is advised. For example, the defibrillator 200 charges the capacitor(s) in response to a charge element 216 receiving a user input signal. The charge element 216 is, for instance, a button. In some examples, the charge element 216 is a user-selectable graphical user interface element displayed on the display screens 201 and 202. According to some implementations, the defibrillator 200 automatically charges the capacitor(s) in response to calculating a shock index less than a first threshold or above a second threshold. In other implementations, the defibrillator 200 automatically charges the capacitor in response to calculating a shock index above a first threshold and below a second threshold.

In some implementations, the defibrillator 200 administers a defibrillation shock to the individual in response to an input signal from the user. For example, the defibrillator 200 outputs the defibrillation shock based on a user input signal received by a shock element 218. The defibrillator 200 outputs the defibrillation shock by discharging the charged capacitor(s). The shock element 218 is, for instance, a button. In some cases, the shock element 218 outputs a signal (e.g., a light signal or aural signal) when the capacitor(s) is charged. In some implementations, the shock element 218 is a user-selectable graphical user interface displayed on the display screens 201 and 202.

Figure 3:
FIG. 3 illustrates example signaling for facilitating communication between medical devices.

FIG. 3 illustrates example signaling 300 for facilitating communication between medical devices. In particular, the signaling 300 is between the monitoring device 106, sensor 108, and treatment device 110 described above with reference to FIG. 1. Various messages within the signaling 300 are transmitted over at least one wired connection and/or at least one wireless connection. Although not specifically illustrated, various messages within the signaling 300 are transmitted via one or more intermediary devices.

The monitoring device 106 receives a parameter signal 302 from the sensor 108. The parameter signal 302 indicates one or more physiological parameters of a subject, such as a patient. For example, the parameter signal 302 includes at least one of an ECG, a transthoracic impedance, an airway parameter (e.g., a flow rate, a partial pressure of oxygen, a partial pressure of carbon dioxide, a capnograph, and end tidal parameter (e.g., $EtCO2$), etc.), a blood pressure, a blood oxygenation (e.g., regional oximetry, pulse oximetry, etc.), a cerebral regional tissue oxygen saturation, a CPR position, or the like. In various cases, the sensor 108 includes at least one of an electrode, a detection circuit, a flow sensor, an oxygen sensor, a carbon dioxide sensor, a non-invasive blood pressure (NIBP) sensor (e.g., a blood pressure cuff, an ultrasound-based blood pressure sensor, etc.), an oxygenation sensor (e.g., a regional oximetry sensor, a pulse oximetry sensor), or the like. In some implementations the monitoring device 106 includes the sensor 108.

The parameter signal 302, according to various examples, further indicates a treatment being performed on the subject by the treatment device 110. For example, the parameter signal 302 indicates at least one of chest compressions, a ventilation treatment, a defibrillation treatment, a pacing treatment, or a medication being administered by the treatment device 110 to the subject. In various cases, the treatment is indicated by an artifact present in the parameter signal 302. For instance, if the parameter signal 302 is an ECG, a chest compression artifact in the ECG indicates the administration of chest compressions to the subject. In various implementations, the monitoring device 106 identifies the treatment by analyzing the parameter signal 302. For instance, the monitoring device 106 determines a frequency and/or timing of the treatment by analyzing the parameter signal 302.

In various implementations, the monitoring device 106 and the treatment device 110 exchange substantive data. In various implementations, the monitoring device 106 and/or the treatment device 110 exchange one or more report(s)

304. For instance, the report(s) 304 include at least one physiological parameter, at least one treatment parameter, or a combination thereof.

In some cases, the monitoring device 106 and/or the treatment device 110 exchange one or more instructions 306. In some cases, the instruction(s) 306 include at least one instruction to measure a physiological parameter, to begin a treatment, to end a treatment, a particular time or frequency at which to perform an action, an instruction to power on, an instruction to power off, an instruction to disconnect from a patient being treated or monitored, or a combination thereof.

In various cases, the monitoring device 106 confirms that the treatment device 110 is treating the subject that the monitoring device 106 is monitoring. For example, the monitoring device 106 determines that the treatment indicated by the report(s) 304 is consistent with the treatment and/or that the treatment elicited an effect as indicated by the parameter signal 302.

Data is transmitted between the monitoring device 106, the sensor 108, and the treatment device 110 asynchronously and/or synchronously. In some implementations, the sensor 108 transmits an example parameter signal 302 and/or the treatment device 110 transmits an example report among the report(s) 304. In particular implementations, the monitoring device 106 transmits instruction(s) 306 to the treatment device 110 to administer, refrain from, or adjust treatment. For instance, the monitoring device 106, in response to determining that the physiological parameter is outside of a predetermined range (e.g., the parameter is greater than a first threshold or lower than a second threshold), can send instruction(s) 306 to the treatment device 110 to pause chest compressions. In some implementations, the monitoring device 106, in response to determining that the physiological parameter is less than a first threshold or above a second threshold) or in response to user input, can transmit instruction(s) 306 to the treatment device 110 to administer an electrical shock In particular implementations, the monitoring device 106 transmits a report 304 indicating a physiological parameter of the subject in response to determining that the physiological parameter is outside of a predetermined range (e.g., the parameter is greater than a first threshold or lower than a second threshold). In some instances, the treatment device 110 transmits an instruction to measure a physiological parameter in response to determining that the treatment is complete. For instance, the treatment device 110 instructs the monitoring device 106 to detect an ECG of the subject in response to the treatment device 110 pausing chest compressions. In some implementations, the treatment device 110 periodically transmits reports indicating an ongoing treatment of the subject, such as every ten seconds. In some cases, the monitoring device 106 periodically transmits instructions to adjust the treatment based on real-time conditions of the monitored subject.

FIG. 4 illustrates an example process 400 for managing inconclusive results in analysis of a physiological parameter. The example process 400 is performed by an entity, such as the monitoring device 106, the defibrillator 200, a medical device, a processor executing instructions, or a combination thereof.

At 402, the entity generates first filtered data by applying a first filter to data representing a physiological parameter. In some implementations, the first filter includes an adaptive filter, an inverse comb filter, a high-pass filter, a band reject filter, a FIR filter, an (IIR filter, or any combination thereof. In some implementations, the physiological parameter includes an ECG, a transthoracic impedance, a blood pressure, a cerebral regional tissue oxygen saturation, or an EtCO2.

At 404, the entity determines an index by analyzing the first filtered data.

At 406, the entity determines that the index is greater than a first threshold and lower than a second threshold. In some cases, the entity further outputs an alert based on determining that the index is greater than the first threshold and lower than the second threshold. In particular implementations, the alert is a visual or aural alert. In particular implementations, a visual alert can be presented on a display or screen. In some implementations, the aural alert is output from a speaker.

At 408, the entity generates second filtered data by applying a second filter to the data representing the physiological parameter. In some implementations, the second filter includes a comb filter.

At 410, the entity displays the second filtered data for a predetermined time period. Upon expiration of the predetermined time period after displaying the second filtered data, the entity further repeats the process by determining a second index by analyzing the first filtered data, generating a treatment recommendation by analyzing the second index, and displaying the first treatment recommendation. In alternative cases, before expiration of the predetermined time after outputting the second filtered data, the entity causes the display to visually present an option to initiate generation of the second index. In some implementations, the treatment recommendation is to initiate an electrical shock. In alternative cases, the treatment recommendation is to refrain from initiating an electrical shock.

In some cases, the entity includes a discharge circuit configured to output an electrical shock to the subject and an input device. In some cases, upon determining that the second index is greater than the first threshold and lower than the second threshold, the entity is further configured to cause the display to visually present the second filtered data. Further, the entity then determines that the input device has received an input signal indicating a request to administer an electrical shock to the subject and cause a discharge circuit to output an electrical shock to the subject.

In some cases, the entity includes a transceiver configured to communicate a signal to a mechanical chest compression device administering chest compressions to the subject. In some cases, the transceiver is configured to receive a signal from a mechanical chest compression, the signal indicating a frequency of the chest compressions. In some implementations, upon determining that the second index is greater than the first threshold and lower than the second threshold, the entity further sends a signal to a mechanical chest compression device to pause chest compressions. While chest compressions are paused, the entity can determine a third index by analyzing the first filtered data and generate a second treatment recommendation by analyzing the third index. In particular implementations, the entity causes the display to visually present the second treatment recommendation.

In some implementations, the entity includes a sensor configured to detect the physiological parameter of a subject. In some implementations, the entity includes a display. In some implementations, the subject is receiving chest compression from a mechanical chest compression device. In some implementations, the entity includes an analog to digital converter (ADC) configured to convert an ECG to unfiltered data.

FIG. 5 illustrates an example process 500 for managing treatment output based on multiple instruction inputs. The example process 500 is performed by an entity, such as the monitoring device 106, the defibrillator 200, a medical device, a processor executing instructions, or a combination thereof.

At 502, the entity determines an index by analyzing first data indicating a physiological parameter of a subject during a first time period. In some implementations, a physiological parameter includes an ECG, a transthoracic impedance, a blood pressure, a cerebral regional tissue oxygen saturation, or an EtCO2

At 504, the entity determines that the index is less than a first threshold or above a second threshold. In some implementations, determining that the index is less than the first threshold or above the second threshold includes determining that the physiological parameter is indicative of VF or VT.

At 506, the entity displays a recommendation to administer the treatment. In some cases, the entity displays the recommendation on an output device. In some cases, the output device includes a display, haptic output device, a printer, or any combination thereof.

At 508, the entity receives an input signal indicating a request to administer the treatment. In some cases, the input signal is received by the entity from an input device.

At 510, the entity causes the treatment component to prepare the treatment during a second time period. In some implementations, a subject is receiving chest compressions during the second time period. In some cases, the treatment is an electrical shock. In some implementations, the entity prepares the treatment, the treatment being an electrical shock, by charging a capacitor.

At 512, the entity determines that the second data indicating the physiological parameter of the subject during second time period is indicative of a non-pathologic condition. In some implementations, the index is a first index and the entity determines that the second data is indicative of the non-pathologic condition by determining a second index by analyzing the second data and determining that the second index is below the first threshold or above the second threshold. In some cases, the entity outputs an alert upon determining that the second data is indicative of the non-pathologic condition. The alert, for instance, can be a visual alert or an audible alert. In some implementations, the entity includes a speaker configured to output the audible alert. In some implementations, the entity includes a display or light to output the visual alert. In some cases, the non-pathologic condition is indicative of QRS complexes.

At 514, the entity causes the treatment component to refrain from outputting the treatment. In some cases, the entity further displays a selectable option to discharge a voltage stored in the treatment component.

In other implementations, the index is a first index, the recommendation is a first recommendation, the input signal is a first input signal, and the entity further determines a second index by analyzing third data indicating the physiological parameter of the subject in response to causing the treatment component to refrain from outputting the treatment to the subject. In some cases, the entity determines that the second index is below the first threshold or above the second threshold and thereby displays a second recommendation to administer the treatment to the subject. In some cases, the entity determines that the input device has received a second input signal indicating a request to administer the treatment to the subject in response to displaying the second recommendation and thereby causes the treatment component to charge during a fourth time period, wherein the subject is receiving chest compression during the fourth time period. In some cases, the entity determines a third index by analyzing the physiological parameter of the subject during the fourth time period, determines that the third index is below the first threshold or above the second threshold, and thereby cause the treatment component to output the treatment to the subject.

In some implementations, the physiological parameter includes an ECG, a transthoracic impedance, an airway parameter, a blood oxygenation, or a blood pressure. In some implementations, the treatment includes an electrical shock, chest compressions, or ventilation. In some implementations, the entity includes a detection circuit configured to detect a physiological parameter of the subject, a treatment component configured to output a treatment to the subject, and/or an input device. In some cases, the treatment component includes a discharge circuit configured to output an electrical shock to the subject.

FIG. 6 illustrates an example process 600 for identifying a shockable arrhythmia in ECG data that includes a chest compression artifact. The process 600 is performed by an entity, such as the monitoring device 106 described above with reference to FIG. 1, a defibrillator 200 described above with reference to FIG. 1, a medical device, a monitor-defibrillator, a processor or any combination thereof. In some examples, the example process 600 is performed during an analysis period.

At 602, the entity identifies a segment of ECG data representing an electrical activity of an individual's heart when the individual is receiving chest compressions. The ECG data is obtained by detecting one or more relative voltages between electrodes connected to the chest of the individual, for instance. The ECG data is digital data representing the detected voltages, for example. According to various implementations, the chest compressions generate noise in the ECG data. The noise is at least partly based on jostling or movement of the electrodes on the skin of the individual, for example. An artifact is present in the ECG data based on the chest compressions. If the raw ECG data is output to a user, the chest compression artifact makes the ECG data difficult for the user to evaluate, in some cases. For instance, the user may have difficulty manually discerning whether a shockable arrhythmia (e.g., VF or pulseless VT) is present in the ECG data. Accordingly, the entity removes the artifact and automatically determines whether the shockable arrhythmia is present.

The segment is selected from the ECG data. As used herein, the term "segment" can refer to a subset of data that are obtained from a first time to a second time, wherein the first time occurs after the time of the first datapoint in the data and/or the second time occurs before the time of the last datapoint in the data. In some cases, the data in the segment are obtained over a time interval. The time interval, for example, is at least a minimum period and no longer than a maximum period. The minimum period, for instance, is 3 seconds, 4 seconds, 8 seconds, 10 seconds, or another time interval. The maximum period, for example, is 12 seconds, 20 seconds, 30 seconds, or some other time interval. In some cases, the segment includes a pre-charge time period, wherein the capacitor has not been charged. In other cases, the segment includes a time period necessary to charge the capacitor. In still other cases, the segment includes a CPR period. In some cases, the segment includes time period in which chest compressions are paused.

At 604, the entity identifies chest compressions administered to the individual. In some cases, the entity determines when the chest compressions are administered based on a signal from a chest compression monitor, which in some cases is disposed on the chest of the individual includes at least one accelerometer and/or gyroscope that detects chest compressions administered to the individual. In some examples, the entity detects an electrical impedance between two or more electrodes in contact with the individual and determines when the chest compressions are administered based on the electrical impedance. The chest compressions are administered to the individual during a time period at which the segment of the ECG data is detected, such that the chest compressions cause the chest compression artifact.

At 606, the entity generates filtered ECG data by removing the chest compression artifact of the selected segment of the ECG data. The chest compression artifact has a fundamental that is between 1.5 to 2 Hz, in various examples. However, heart rhythm features (e.g., a VF rhythm, a VT rhythm, QRS complexes, and other inherent heart rhythms) are typically defined by higher frequencies. In some examples, the entity applies a filter to the detected ECG segment, such as an adaptive filter (e.g., a Wiener filter, a Kalman filter, or the like), an nth order filter (e.g., a zero-th order filter) a comb filter, an inverse comb filter, a high-pass filter, a band reject filter, a FIR filter, an IIR filter, or a combination thereof. In some cases, the entity converts the ECG segment from the time domain into the frequency (e.g., a Fourier) domain, a Laplace domain, a Z-transform domain, or a wavelet (e.g., a continuous wavelet transform, a discrete wavelet transform, etc.) domain, and removes at least a portion of the chest compression artifact by processing the converted ECG. According to some examples, the entity identifies and subtracts the chest compression artifact. For instance, the entity identifies and subtracts the chest compression artifact based on the detected chest compressions. For example, the entity cross-correlates the ECG segment with data corresponding to the chest compressions (e.g., the impedance, the acceleration of the compression detector, the velocity of the compression detector, etc.), identifies the chest compression artifact based on the cross-correlation, and subtracts the chest compression artifact from the ECG segment. In some instances, the entity denoises the ECG segment. For example, the entity removes at least a portion of the chest compression artifact by performing spectral subtraction on the ECG segment.

Optionally, the entity applies additional filtering techniques to reduce the harmonics of the chest compression artifact in the selected segment of the ECG data. For example, the entity applies a comb filter with multiple stopbands that correspond to the fundamental frequency of the chest compressions administered to the individual and one or more harmonics of the fundamental frequency.

At 608, the entity calculates a shock index based on the filtered ECG data. The shock index, for example, corresponds to a likelihood that the original ECG data and/or the filtered ECG data exhibits a rhythm that is treatable with defibrillation. For example, the shock index relates to the likelihood that the filtered ECG data is indicative that the individual is exhibiting VF or pulseless VT. In some examples, the entity calculates the shock index by detecting a shockable arrhythmia (e.g., VF or pulseless VT) in the filtered ECG data. In some cases, the entity performs a rules-based analysis on the filtered ECG data. In some examples, the shock index is generated based on an amplitude magnitude spectrum area (AMSA) of the filtered ECG data, an amplitude of the filtered ECG data, a frequency of the filtered ECG data, or a combination thereof. In some implementations, the entity calculates the shock index by determining a spectral similarity between the filtered ECG and a sample ECG with a known shockable arrhythmia (e.g., VF or pulseless VT) and/or by determining a spectral dissimilarity between the filtered ECG and a sample ECG with a known nonshockable rhythm (e.g., asystole, a sinus rhythm including QRS complexes, etc.). In some examples the entity uses non-ECG data to generate the shock index, at least in part. For instance, the entity generates the shock index based on a non-ECG physiological parameter (e.g., a heart rate level or waveform, a temperature level or waveform, an airway $CO_2$ level or waveform, an oxygenation level or waveform, a blood pressure level or waveform, etc.) of the individual, a type of equipment monitoring the individual, a demographic of the individual, or a combination thereof. In some examples, the shock index is calculated based on a regression (e.g., linear regression, binary regression, polynomial regression, logistic regression, nonlinear regression, nonparametric regression, etc.) model outputting a probability that the filtered ECG exhibits a shockable arrhythmia based on one or more characteristics of the filtered ECG. In various implementations, the entity generates the shock index based on one or more analysis factors.

At 610, the entity determines whether the shock index is less than a first threshold. The first threshold is selected, for instance, based on an acceptable level of uncertainty regarding a nonshockable recommendation. In some cases, the first threshold is user-selected, such that the first threshold is calculated based on an input signal from a user. In some cases, the entity determines the first threshold based on one or more analysis factors. If the entity determines that the shock index is less than the first threshold, the entity returns a nonshockable recommendation at 612.

If, on the other hand, the entity determines that the shock index is greater than or equal to the first threshold, the process 600 proceeds to 614. At 614, the entity determines whether the shock index is greater than the second threshold. The second threshold is selected, for instance, based on an acceptable level of uncertainty regarding a shockable recommendation. In some cases, the second threshold is user-selected, such that the second threshold is calculated based on an input signal from a user. In some examples, the entity determines the second threshold based on one or more analysis factors. If the entity determines that the shock index is greater than the second threshold, the entity returns a shockable recommendation at 616.

However, if the entity determines that the shock index is less than or equal to the second threshold, then the entity returns an indeterminate recommendation at 618. The indeterminate decision means that the entity is unable to conclude whether the shockable arrhythmia is present with a sufficient level of certainty. The level of certainty, in some cases, is predetermined and/or selected by a user.

In various cases, the entity performs the process 600 repeatedly, periodically, or a combination thereof. For example, upon returning a recommendation, the entity repeats the process 600 by identifying another segment of ECG data. In some cases, the entity initiates the process 600 (e.g., begins 602) at a particular frequency, such that the entity may be performing the process 600 multiple times, in parallel, at a time. If the entity determines multiple recommendations based on repeatedly and/or periodically performing the process 600, the entity outputs (e.g., to the user) a recommendation based on the most recently returned shock decision.

Figure 7:
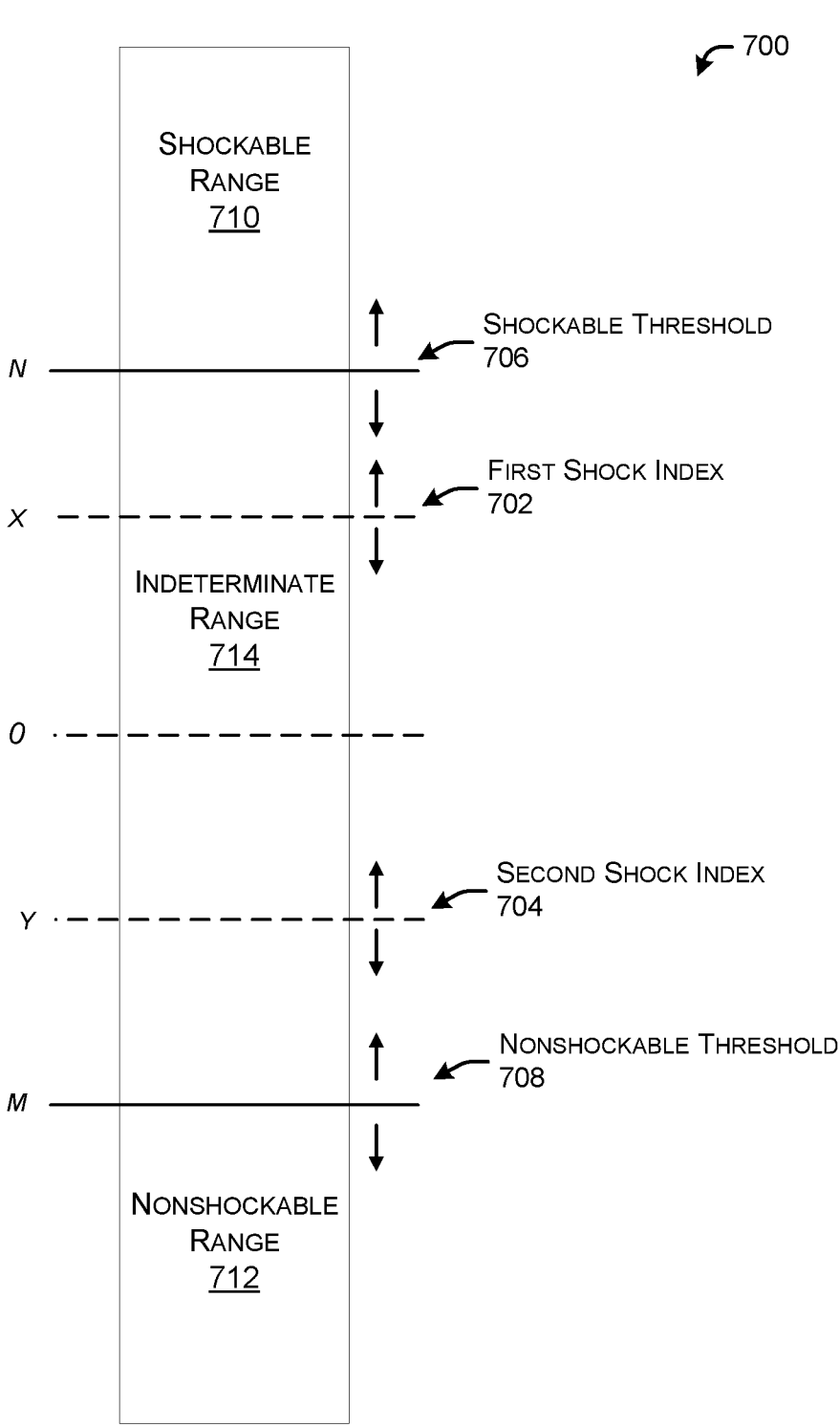
FIG. 7 is a diagram illustrating examples of possible shock index and threshold adjustments.

FIG. 7 is a diagram 700 illustrating examples of possible shock index and threshold adjustments. In various examples, a medical device, such as the monitoring device 106 described above with reference to FIG. 1, the defibrillator 200 as described above with reference to FIGS. 2A and 2B, a monitor-defibrillator, a processor, or any combination thereof, calculates a shock index of an individual based on a computing model (e.g., a regression) model that accepts various ECG features and/or other analysis factors as inputs and provides a shock index as an output.

In various implementations, a medical device (such as the monitoring device 106 described above with reference to FIG. 1, the defibrillator 200 as described above with reference to FIGS. 2A and 2B, a monitor-defibrillator, a processor, or any combination thereof) calculates a shock index (e.g., a first shock index 702 or a second shock index 704) of an ECG segment of an individual based on the computing model. In various examples, the medical device calculates and/or adjusts the shock index based on one or more analysis factors. These analysis factors, in some implementations, change the position of the shock index in the diagram 700. Examples of analysis factors include whether the ECG of the individual previously exhibited high-amplitude VF within a particular time period, whether the individual is a child or an adult, a non-ECG physiological parameter of the individual, whether the individual has exhibited a pulse within a particular time period, whether chest compressions have been administered during a pause period, whether steepness of slopes in the ECG have decreased over time, based on a range and/or trend of shock indices corresponding to previous segments of the ECG, or a combination thereof.

For example, the medical device determines the shock index based on determining that a chest compression device is administering chest compressions to the individual, rather than a human rescuer. In some cases, the medical device determines the shock index based on determining that the ECG has exhibited high-amplitude VF within a particular time period. In some examples, the medical device determines the shock index based on determining that the individual is a child, rather than an adult. In some instances, the medical device determines the shock index based on a physiological parameter of the individual. In some implementations, the medical device determines the shock index based on determining that chest compressions were administered to the individual during a previous pause period. In some examples, the medical device determines the shock index based on determining that a steepness of slopes of the ECG has decreased over time. In some instances, the medical device determines the shock index based on a range and/or trend of shock indices corresponding to previous segments of the ECG. In some cases, the medical device determines the shock index based on whether the medical device has previously administered a shock to the individual (e.g., within a particular time period, such as a five-minute time period ending when the medical device determines the shock index).

In various examples, the medical device determines whether to decide and/or recommend administration of a defibrillation shock to the individual based upon a comparison between the shock index and a shockable threshold 706 and a comparison between the shock index and a nonshockable threshold 708. In some examples, the shockable threshold 706 and the nonshockable threshold 708 are derived based on a pre-specified certainty. For example, the shockable threshold 706 and/or the nonshockable threshold 708 correspond to a particular probability that a positive shock index indicates a shockable arrhythmia or a negative shock index indicates a nonshockable rhythm. The probability is, for instance, between 80% and 99%. In some cases, the medical device receives an input signal indicative of the probability.

In some implementations, the medical device outputs a signal indicative of the probability to a user. For example, the medical device determines that the ECG has an a % likelihood of exhibiting a shockable arrhythmia (e.g., VF or pulseless VT) or determines that the ECG has a b % likelihood of exhibiting a nonshockable rhythm (e.g., asystole, sinus rhythm, pulsatile VT, etc.). The medical device, for example, determines the a % or b % based on the comparison between the shock index and the shockable threshold 706 or based on the comparison between the shock index and the nonshockable threshold 708. In some examples, the medical device communicates the a % probability or the b % probability to the user. For instance, the medical device outputs a visual signal or an audible signal indicative of the a % probability or the b % probability by a screen or a speaker.

If the shock index of the individual is greater than the shockable threshold 706, for instance, the medical device determines that the ECG segment includes a shockable arrhythmia (i.e., a shock index within the shockable range 710 (e.g., VF or pulseless VT)) and a defibrillation shock is indicated. For example, if the first shock index 702 is generated based on the ECG segment, the first shock index 702 is equal to X, the shockable threshold 706 is equal to N, and X>N, then the medical device determines that the ECG segment is indicative of a shockable arrhythmia. If the shock index of the individual is less than the nonshockable threshold 708, then the medical device determines that the ECG segment includes a nonshockable rhythm (i.e., a shock index within the nonshockable range 712 (e.g., asystole, a rhythm including QRS complexes, etc.)). For example, if the second shock index 704 is generated based on the ECG segment, the second shock index 704 is equal to Y, the nonshockable threshold 708 is equal to M, and M>Y, then the medical device determines that the ECG segment is indicative of a nonshockable rhythm.

An indeterminate range 714 is defined between the shockable threshold 706 and the nonshockable threshold 708. If the shock index of the individual is within an indeterminate range 714, such that the shock index is greater than the nonshockable threshold 708 and less than the shockable threshold 706, then the medical device is unable to determine, with sufficient certainty, whether the ECG segment includes a shockable arrhythmia or a nonshockable rhythm. For example, if the first shock index 702 is generated based on the ECG segment, the first shock index 702 is equal to X, the shockable threshold 706 is equal to N, the nonshockable threshold 708 is M, and N>X>M, then the medical device determines that the ECG segment is indeterminate. In some examples, the medical device outputs a recommendation based on whether the ECG segment includes the shockable arrhythmia, the nonshockable rhythm, or is indeterminate.

In some examples, the medical device adjusts the shockable threshold 706 and/or the nonshockable threshold 708 based on an analysis factor. For example, the medical device adjusts the shockable threshold 706 and/or the nonshockable threshold 708 based on whether the ECG of the individual previously exhibited high-amplitude VF within a particular time period, whether the individual is a child or an adult, a non-ECG physiological parameter of the individual, whether the individual has exhibited a pulse within a particular time period, whether chest compressions have been administered during a pause period, whether steepnesses of slopes in the ECG have decreased over time, based on a range and/or trend of shock indices corresponding to previous segments of the ECG, or a combination thereof.

The adjustment to the shockable threshold 706 and/or the nonshockable threshold 708 is symmetric or asymmetric. For example, in some cases, the medical device adjusts both of the shockable threshold 706 and the nonshockable threshold 708 symmetrically, such that any increase in the shockable threshold 706 corresponds to a decrease in the nonshockable threshold 708, or vice versa. For example, if the individual is a child, the medical device may decrease the shockable threshold 706 and increase the nonshockable threshold 708 symmetrically. Similarly, if the medical device determines that chest compressions have been previously administered during a pause period, the medical device may decrease the shockable threshold 706 and increase the nonshockable threshold 708 symmetrically. In some cases, the medical device adjusts the shockable threshold 706 and/or the nonshockable threshold 708 asymmetrically, such that any increase in the shockable threshold 706 is asymmetric with any decrease, if any, in the nonshockable threshold 708, or vice versa. An asymmetric adjustment in the shockable threshold 706 and the nonshockable threshold 708 is appropriate when the medical device concludes, based on an analysis factor, that a certainty of the shockable decision should be different than a certainty of the nonshockable decision. For instance, if the medical device determines that the individual previously exhibited high-amplitude VF, the medical device may asymmetrically increase the nonshockable threshold 708.

Figure 8:
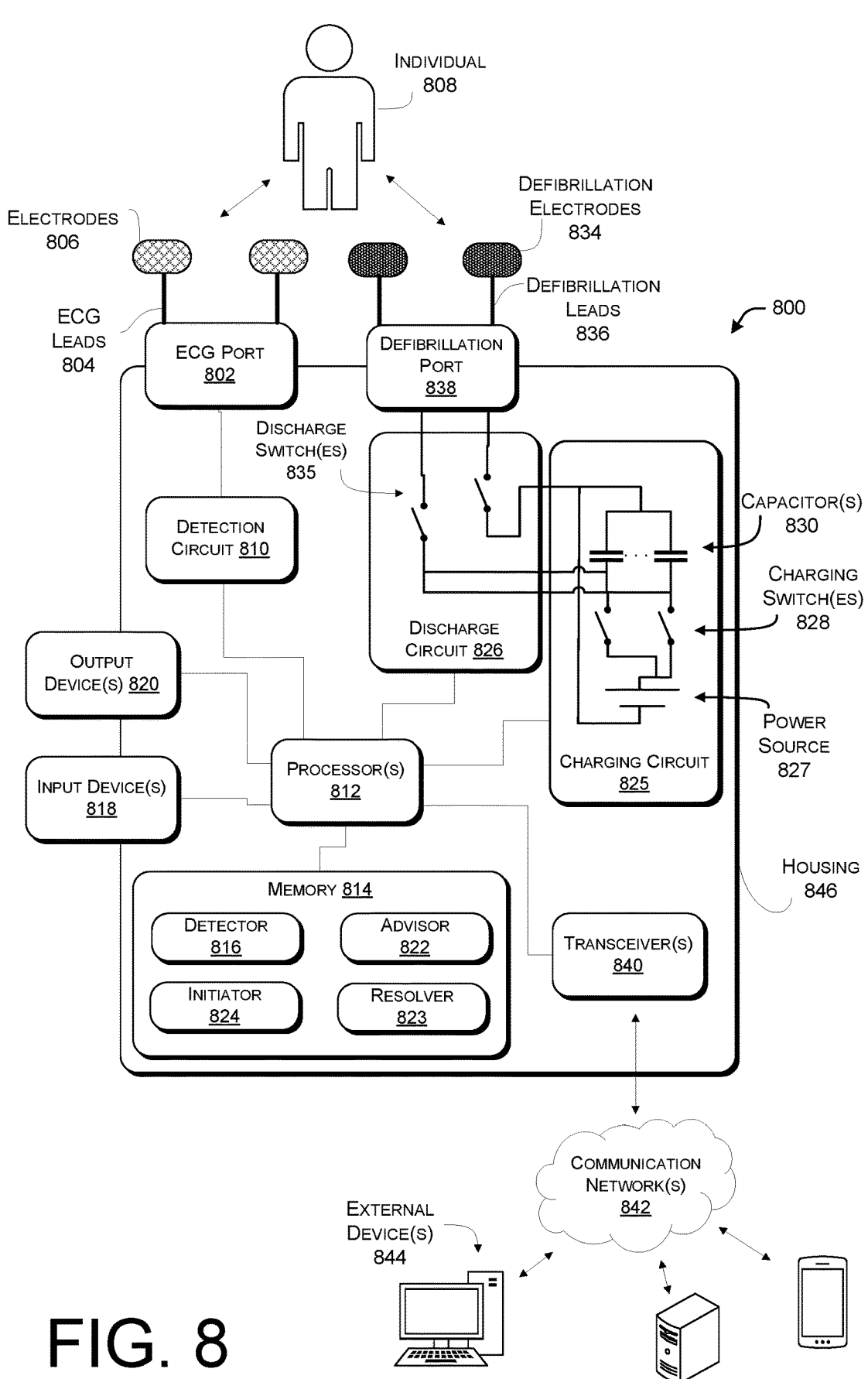
FIG. 8 illustrates an example of an external defibrillator configured to perform various functions described herein.

FIG. 8 illustrates an example of an external defibrillator 800 configured to perform various functions described herein. For example, the external defibrillator 800 is the monitoring device 106 described above with reference to FIG. 1 and/or the defibrillator 200 described above with reference to FIGS. 2A and 2B.

The external defibrillator 800 includes an ECG port 802 connected to multiple ECG leads 804. In some cases, the ECG leads 804 are removable from the ECG port 802. For instance, the ECG leads 804 are plugged into the ECG port 802. The ECG leads 804 are connected to ECG electrodes 806, respectively. In various implementations, the ECG electrodes 806 are disposed on different locations on an individual 808. A detection circuit 810 is configured to detect relative voltages between the ECG electrodes 806. These voltages are indicative of the electrical activity of the heart of the individual 808.

In various implementations, the ECG electrodes 806 are in contact with the different locations on the skin of the individual 808. In some examples, a first one of the ECG electrodes 806 is placed on the skin between the heart and right arm of the individual 808, a second one of the ECG electrodes 806 is placed on the skin between the heart and left arm of the individual 808, and a third one of the ECG electrodes 806 is placed on the skin between the heart and a leg (either the left leg or the right leg) of the individual 808. In these examples, the detection circuit 810 is configured to measure the relative voltages between the first, second, and third ECG electrodes 806. Respective pairings of the ECG electrodes 806 are referred to as "leads," and the voltages between the pairs of ECG electrodes 806 are known as "lead voltages." In some examples, more than three ECG electrodes 806 are included, such that 5-lead or 12-lead ECG signals are detected by the detection circuit 810.

The detection circuit 810 includes at least one analog circuit, at least one digital circuit, or a combination thereof. The detection circuit 810 receives the analog electrical signals from the ECG electrodes 806, via the ECG port 802 and the ECG leads 804. In some cases, the detection circuit 810 includes one or more analog filters configured to filter noise and/or artifact from the electrical signals. The detection circuit 810 includes an analog-to-digital (ADC) in various examples. The detection circuit 810 generates a digital signal indicative of the analog electrical signals from the ECG electrodes 806. This digital signal can be referred to as an "ECG signal" or an "ECG."

In some cases, the detection circuit 810 further detects an electrical impedance between at least one pair of the ECG electrodes 806. For example, the detection circuit 810 includes, or otherwise controls, a power source that applies a known voltage (or current) across a pair of the ECG electrodes 806 and detects a resultant current (or voltage) between the pair of the ECG electrodes 806. The impedance is generated based on the applied signal (voltage or current) and the resultant signal (current or voltage). In various cases, the impedance corresponds to respiration of the individual 808, chest compressions performed on the individual 808, and other physiological states of the individual 808. In various examples, the detection circuit 810 includes one or more analog filters configured to filter noise and/or artifact from the resultant signal. The detection circuit 810 generates a digital signal indicative of the impedance using an ADC. This digital signal can be referred to as an "impedance signal" or an "impedance."

The detection circuit 810 provides the ECG signal and/or the impedance signal one or more processor(s) 812 in the external defibrillator 800. In some implementations, the processor(s) 812 includes a central processing unit (CPU), a graphics processing unit (GPU), both CPU and GPU, or other processing unit or component known in the art.

The processor(s) 812 is operably connected to memory 814. In various implementations, the memory 814 is volatile (such as random access memory (RAM)), non-volatile (such as read only memory (ROM), flash memory, etc.) or some combination of the two. The memory 814 stores instructions that, when executed by the processor(s) 812, causes the processor(s) 812 to perform various operations. In various examples, the memory 814 stores methods, threads, processes, applications, objects, modules, any other sort of executable instruction, or a combination thereof. In some cases, the memory 814 stores files, databases, or a combination thereof. In some examples, the memory 814 includes, but is not limited to, RAM, ROM, electrically erasable programmable read-only memory (EEPROM), flash memory, or any other memory technology. In some examples, the memory 814 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 812 and/or the external defibrillator 800. In some cases, the memory 814 at least temporarily stores the ECG signal and/or the impedance signal.

In various examples, the memory 814 includes a detector 816, which causes the processor(s) 812 to determine, based on the ECG signal and/or the impedance signal, whether the individual 808 is exhibiting a particular heart rhythm. For instance, the processor(s) 812 determines whether the individual 808 is experiencing a shockable arrhythmia that is treatable by defibrillation. Examples of shockable arrhythmias include VF and VT. In some examples, the processor(s)

812 determines whether any of a variety of different rhythms (e.g., asystole, sinus rhythm, atrial fibrillation (AF), etc.) are present in the ECG signal.

The processor(s) 812 is operably connected to one or more input device(s) 818 and one or more output device(s) 820. Collectively, the input device(s) 818 and the output device(s) 820 function as an interface between a user and the external defibrillator 800. The input device(s) 818 is configured to receive an input from a user and includes at least one of a keypad, a cursor control, a touch-sensitive display, a voice input device (e.g., a speaker), a haptic feedback device, or any combination thereof. The output device(s) 820 includes at least one of a display, a speaker, a haptic output device, a printer, or any combination thereof. In various examples, the processor(s) 812 causes a display among the input device(s) 818 to visually output a waveform of the ECG signal and/or the impedance signal. In some implementations, the input device(s) 818 includes one or more touch sensors, the output device(s) 820 includes a display screen, and the touch sensor(s) are integrated with the display screen. Thus, in some cases, the external defibrillator 800 includes a touchscreen configured to receive user input signal(s) and visually output physiological parameters, such as the ECG signal and/or the impedance signal.

In some examples, the memory 814 includes an advisor 822, which, when executed by the processor(s) 812, causes the processor(s) 812 to generate advice and/or control the output device(s) 820 to output the advice to a user (e.g., a rescuer). In some examples, the processor(s) 812 provides, or causes the output device(s) 820 to provide, an instruction to perform CPR on the individual 808. In some cases, the processor(s) 812 evaluates, based on the ECG signal, the impedance signal, or other physiological parameters, CPR being performed on the individual 808 and causes the output device(s) 820 to provide feedback about the CPR in the instruction. According to some examples, the processor(s) 812, upon identifying that a shockable arrhythmia is present in the ECG signal, causes the output device(s) 820 to output an instruction and/or recommendation to administer a defibrillation shock to the individual 808.

In some implementations, the memory 814 further includes a resolver 823 which, when executed by the processor(s) 812, causes the processor(s) 812 to perform operations in response to determining that an ECG rhythm analysis is inconclusive. In some cases, the resolver 823 causes the processor(s) 812 to cause the output device(s) 820 to display a second filtered data in response to determining that a shock index of a first filtered data results in an inconclusive determination. In some implementations, the resolver 823 causes the processor(s) 812 to perform operations in response to determining that an ECG rhythm analysis of a first analysis time period disagrees with an ECG rhythm analysis of a second analysis time period. In some cases, a first ECG rhythm analysis results in a shockable determination and a second ECG rhythm analysis results in a nonshockable determination or an indeterminate result. As such, the resolver 823 determines if a non-pathologic condition is present in the ECG and if the non-pathologic condition is not present the resolver 823 causes the processor(s) 812 to administer an electrical shock. In some examples, the resolver 823 includes the analyzer 115 described above with reference to FIG. 1.

The memory 814 also includes an initiator 824 which, when executed by the processor(s) 812, causes the processor(s) 812 to control other elements of the external defibrillator 800 in order to administer a defibrillation shock to the individual 808. In some examples, the processor(s)

812 executing the initiator 824 selectively causes the administration of the defibrillation shock based on determining that the individual 808 is exhibiting the shockable arrhythmia and/or based on an input from a user (received, e.g., by the input device(s) 818. In some cases, the processor(s) 812 causes the defibrillation shock to be output at a particular time, which the processor(s) 812 determines based on the ECG signal and/or the impedance signal.

The processor(s) 812 is operably connected to a charging circuit 825 and a discharge circuit 826. In various implementations, the charging circuit 825 includes a power source 827, one or more charging switche(s) 828, and one or more capacitor(s) 830. The power source 827 includes, for instance, a battery. The processor(s) 812 initiates a defibrillation shock by causing the power source 827 to charge at least one capacitor among the capacitor(s) 830. For example, the processor(s) 812 activates at least one of the charging switch(es) 828 in the charging circuit 825 to complete a first circuit connecting the power source 827 and the capacitor to be charged. Then, the processor(s) 812 causes the discharge circuit 826 to discharge energy stored in the charged capacitor across a pair of defibrillation electrodes 834, which are in contact with the individual 808. For example, the processor(s) 812 deactivates the charging switch(es) 828 completing the first circuit between the capacitor(s) 830 and the power source 827, and activates one or more discharge switches 835 completing a second circuit connecting the charged capacitor(s) 830 and at least a portion of the individual 808 disposed between defibrillation electrodes 834.

The energy is discharged from the defibrillation electrodes 834 in the form of a defibrillation shock. For example, the defibrillation electrodes 834 are connected to the skin of the individual 808 and located at positions on different sides of the heart of the individual 808, such that the defibrillation shock is applied across the heart of the individual 808. The defibrillation shock, in various examples, depolarizes a significant number of heart cells in a short amount of time. The defibrillation shock, for example, interrupts the propagation of the shockable arrhythmia (e.g., VF or VT) through the heart. In some examples, the defibrillation shock is 200 J or greater with a duration of about 0.015 seconds. In some cases, the defibrillation shock has a multiphasic (e.g., biphasic) waveform. The discharge switch(es) 835 are controlled by the processor(s) 812, for example. In various implementations, the defibrillation electrodes 834 are connected to defibrillation leads 836. The defibrillation leads 836 are connected to a defibrillation port 838, in some implementations. According to various examples, the defibrillation leads 836 are removable from the defibrillation port 838. For example, the defibrillation leads 836 are plugged into the defibrillation port 838.

In various implementations, the processor(s) 812 is operably connected to one or more transceiver(s) 840 that transmit and/or receive data over one or more communication network(s) 842. For example, the transceiver(s) 840 includes a network interface card (NIC), a network adapter, a local area network (LAN) adapter, or a physical, virtual, or logical address to connect to the various external devices and/or systems. In various examples, the transceiver(s) 840 includes any sort of wireless transceivers capable of engaging in wireless communication (e.g., radio frequency (RF) communication). For example, the communication network(s) 842 includes one or more wireless networks that include a $3^{rd}$ Generation Partnership Project (3GPP) network, such as a Long Term Evolution (LTE) radio access network (RAN) (e.g., over one or more LE bands), a New Radio (NR) RAN (e.g., over one or more NR bands), or a combination thereof. In some cases, the transceiver(s) 840 includes other wireless modems, such as a modem for engaging in WI-FI®, WIGIG®, WIMAX®, BLUETOOTH®, or infrared communication over the communication network(s) 842.

The external defibrillator 800 is configured to transmit and/or receive data (e.g., ECG data, impedance data, data indicative of one or more detected heart rhythms of the individual 808, data indicative of one or more defibrillation shocks administered to the individual 808, etc.) with one or more external device(s) 844 via the communication network(s) 842. The external device(s) 844 include, for instance, mobile devices (e.g., mobile phones, smart watches, etc.), Internet of Things (IoT) devices, medical devices, computers (e.g., laptop devices, servers, etc.), or any other type of computing device configured to communicate over the communication network(s) 842. In some examples, the external device(s) 844 is located remotely from the external defibrillator 800, such as at a remote clinical environment (e.g., a hospital). According to various implementations, the processor(s) 812 causes the transceiver(s) 840 to transmit data to the external device(s) 844. In some cases, the transceiver(s) 840 receives data from the external device(s) 844 and the transceiver(s) 840 provide the received data to the processor(s) 812 for further analysis.

In various implementations, the external defibrillator 800 also includes a housing 846 that at least partially encloses other elements of the external defibrillator 800. For example, the housing 846 encloses the detection circuit 810, the processor(s) 812, the memory 814, the charging circuit 825, the transceiver(s) 840, or any combination thereof. In some cases, the input device(s) 818 and output device(s) 820 extend from an interior space at least partially surrounded by the housing 846 through a wall of the housing 846. In various examples, the housing 846 acts as a barrier to moisture, electrical interference, and/or dust, thereby protecting various components in the external defibrillator 800 from damage.

In some implementations, the external defibrillator 800 is an AED operated by an untrained user (e.g., a bystander, layperson, etc.) and can be operated in an automatic mode. In automatic mode, the processor(s) 812 automatically identifies a rhythm in the ECG signal, makes a decision whether to administer a defibrillation shock, charges the capacitor(s) 830, discharges the capacitor(s) 830, or any combination thereof. In some cases, the processor(s) 812 controls the output device(s) 820 to output (e.g., display) a simplified user interface to the untrained user. For example, the processor(s) 812 refrains from causing the output device(s) 820 to display a waveform of the ECG signal and/or the impedance signal to the untrained user, in order to simplify operation of the external defibrillator 800.

In some examples, the external defibrillator 800 is a monitor-defibrillator utilized by a trained user (e.g., a clinician, an emergency responder, etc.) and can be operated in a manual mode or the automatic mode. When the external defibrillator 800 operates in manual mode, the processor(s) 812 cause the output device(s) 820 to display a variety of information that may be relevant to the trained user, such as waveforms indicating the ECG data and/or impedance data, notifications about detected heart rhythms, and the like.

Figure 9:
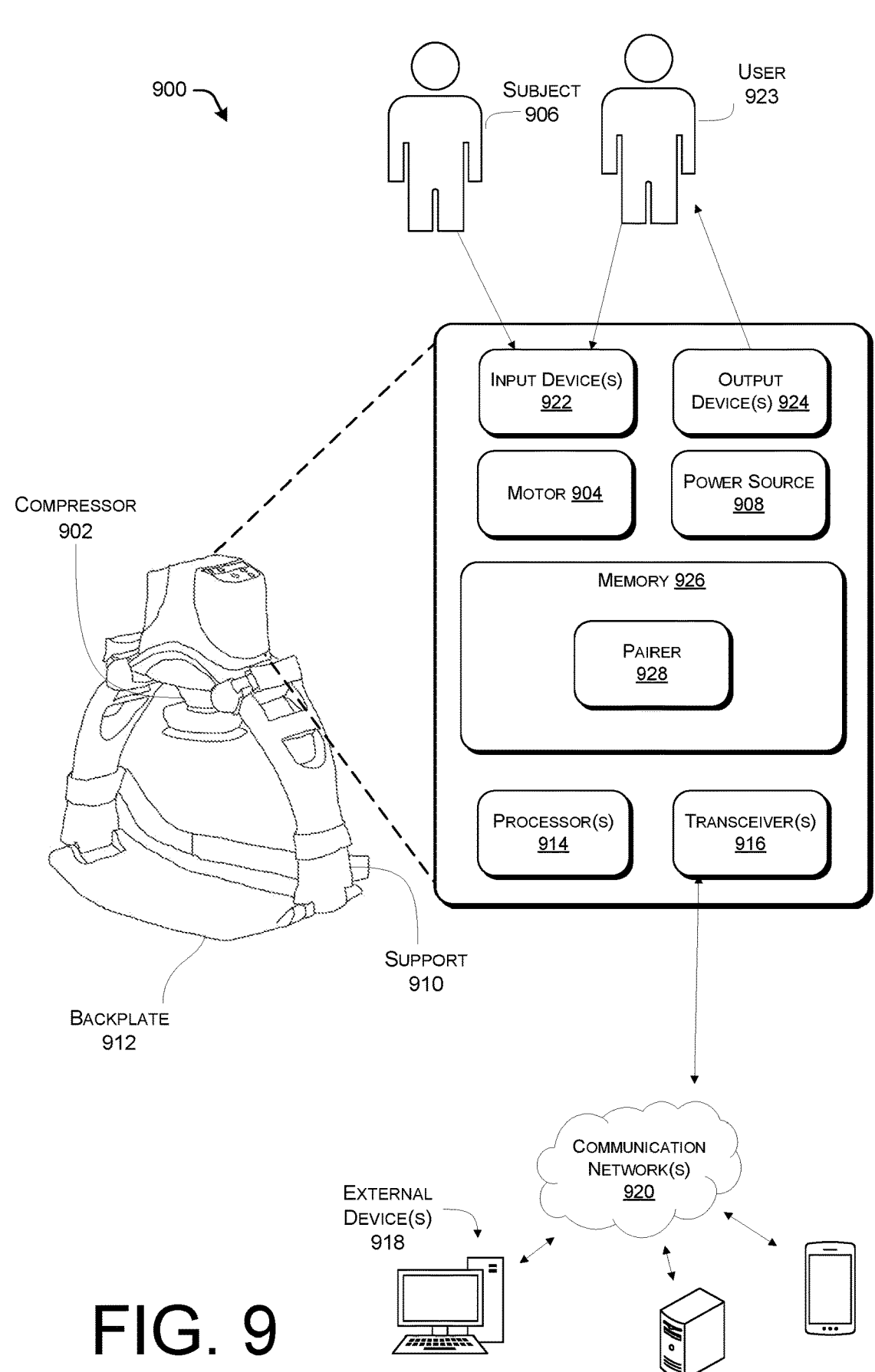
FIG. 9 illustrates a chest compression device configured to perform various functions described herein.

FIG. 9 illustrates a chest compression device 900 configured to perform various functions described herein. For example, the chest compression device 900 is the monitoring device 106, the treatment device 110, the defibrillator

200, the external defibrillator 800, described above with reference to FIGS. 1, 2, and 8.

In various implementations, the chest compression device 900 includes a compressor 902 that is operatively coupled to a motor 904. The compressor 902 physically administers a force to the chest of a subject 906 that compresses the chest of the subject 906. In some examples, the compressor 902 includes at least one piston that periodically moves between two positions (e.g., a compressed position and a release position) at a compression frequency. For example, when the piston is positioned on the chest of the subject 906, the piston compresses the chest when the piston is moved into the compressed position. A suction cup may be positioned on a tip of the piston, such that the suction cup contacts the chest of the subject 906 during operation. In various cases, the compressor 902 includes a band that periodically tightens to a first tension and loosens to a second tension at a compression frequency. For instance, when the band is disposed around the chest of the subject 906, the band compresses the chest when the band tightens. In some implementations, the CPR position includes the compressed position, release position, or some position in between. In some cases, the CPR position is provided by the chest compression device 900.

The motor 904 is configured to convert electrical energy stored in a power source 908 into mechanical energy that moves and/or tightens the compressor 902, thereby causing the compressor 902 to administer the force to the chest of the subject 906. In various implementations, the power source 908 is portable. For instance, the power source 908 includes at least one rechargeable (e.g., lithium-ion) battery. In some cases, the power source 908 supplies electrical energy to one or more elements of the chest compression device 900 described herein.

In various cases, the chest compression device 900 includes a support 910 that is physically coupled to the compressor 902, such that the compressor 902 maintains a position relative to the subject 906 during operation. In some implementations, the support 910 is physically coupled to a backplate 912, cot, or other external structure with a fixed position relative to the subject 906. According to some cases, the support 910 is physically coupled to a portion of the subject 906, such as wrists of the subject 906.

The operation of the chest compression device 900 may be controlled by at least one processor(s) 914. In various implementations, the motor 904 is communicatively coupled to the processor(s) 914. Specifically, the processor(s) 914 is configured to output a control signal to the motor 904 that causes the motor 904 to actuate the compressor 902. For instance, the motor 904 causes the compressor 902 to administer the compressions to the subject 906 based on the control signal. In some cases, the control signal indicates one or more treatment parameters of the compressions. Examples of treatment parameters include a frequency, timing, depth, force, position, velocity, and acceleration of the compressor 902 administering the compressions. According to various cases, the control signal causes the motor 904 to cease compressions.

In various implementations, the chest compression device 900 includes at least one transceiver 916 configured to communicate with at least one external device 918 over one or more communication networks 920. Any communication network described herein can be included in the communication network(s) 920. The external device(s) 918, for example, includes at least one of a monitor-defibrillator, an AED, an ECMO device, a ventilation device, a patient monitor, a mobile phone, a server, or a computing device. In some implementations, the transceiver(s) 916 is configured to communicate with the external device(s) 918 by transmitting and/or receiving signals wirelessly. For example, the transceiver(s) 916 includes a NIC, a network adapter, a LAN adapter, or a physical, virtual, or logical address to connect to the various external devices and/or systems. In various examples, the transceiver(s) 916 includes any sort of wireless transceivers capable of engaging in wireless communication (e.g., RF communication). For example, the communication network(s) 920 includes one or more wireless networks that include a 3GPP network, such as an LTE RAN (e.g., over one or more LTE bands), an NR RAN (e.g., over one or more NR bands), or a combination thereof. In some cases, the transceiver(s) 916 includes other wireless modems, such as a modem for engaging in WI-FI®, WIGIG®, WIMAX®, BLUETOOTH®, or infrared communication over the communication network(s) 920. The signals, in various cases, encode data in the form of data packets, datagrams, or the like. In some cases, the signals are transmitted as compressions are being administered by the chest compression device 900 (e.g., for real-time feedback by the external device(s) 918), after compressions are administered by the chest compression device 900 (e.g., for post-event review at the external device 918), or a combination thereof.

In various cases, the processor(s) 914 generates the control signal based on data encoded in the signals received from the external device(s) 918. For instance, the signals include an instruction to initiate the compressions, and the processor(s) 914 instructs the motor 904 to begin actuating the compressor 902 in accordance with the signals.

In some cases, the chest compression device 900 includes at least one input device 922. In various examples, the input device(s) 922 is configured to receive an input signal from a user 923, who may be a rescuer treating the subject 906. Examples of the input device(s) 922 include, for instance, at a keypad, a cursor control, a touch-sensitive display, a voice input device (e.g., a microphone), a haptic feedback device (e.g., a gyroscope), or any combination thereof. In various implementations, the processor(s) 914 generate the control signal based on the input signal. For instance, the processor(s) 914 generate the control signal to adjust a frequency of the compressions based on the chest compression device 900 detecting a selection by the user 923 of a user interface element displayed on a touchscreen or detecting the user 923 pressing a button integrated with an external housing of the chest compression device 900.

According to some examples, the input device(s) 922 include one or more sensors. The sensor(s), for example, is configured to detect a physiological parameter of the subject 906. In some implementations, the sensor(s) is configured to detect a state parameter of the chest compression device 900, such as a position of the compressor 902 with respect to the subject 906 or the backplate 912, a force administered by the compressor 902 on the subject 906, a force administered onto the backplate 912 by the body of the subject 906 during a compression, or the like. According to some implementations, the signals transmitted by the transceiver(s) 916 indicate the physiological parameter(s) and/or the state parameter(s).

The chest compression device 900 further includes at least one output device 924, in various implementations. Examples of the output device(s) 924 include, for instance, least one of a display (e.g., a projector, an LED screen, etc.), a speaker, a haptic output device, a printer, or any combination thereof. In some implementations, the output device(s) 924 include a screen configured to display various parameters detected by and/or reported to the chest compression device 900, a charge level of the power source 908, a timer indicating a time since compressions were initiated or paused, and other relevant information.

The chest compression device 900 further includes memory 926. In various implementations, the memory 926 is volatile (such as RAM), non-volatile (such as ROM, flash memory, etc.) or some combination of the two. The memory 926 stores instructions that, when executed by the processor(s) 914, causes the processor(s) 914 to perform various operations. In various examples, the memory 926 stores methods, threads, processes, applications, objects, modules, any other sort of executable instruction, or a combination thereof. In some cases, the memory 926 stores files, databases, or a combination thereof. In some examples, the memory 926 includes, but is not limited to, RAM, ROM, EEPROM, flash memory, or any other memory technology. In some examples, the memory 926 includes one or more of CD-ROMs, DVDs, CAM, or other optical storage, magnetic cassettes, magnetic tape, magnetic disk storage or other magnetic storage devices, or any other medium which can be used to store the desired information. In various cases, the memory 926 stores instructions, programs, threads, objects, data, or any combination thereof, that cause the processor(s) 914 to perform various functions. In various cases, the memory 926 stores one or more parameters that are detected by the chest compression device 900 and/or reported to the chest compression device 900.

In implementations of the present disclosure, the memory 926 also stores instructions for executing a pairer 928. In some cases, the processor(s) 914, when executing the pairer 928, generates one or more pairing requests and/or responses that are transmitted, by the transceiver(s) 916, to the external device(s) 918. In some examples, the processor(s) 914, when executing the pairer 928, analyzes one or more pairing requests and/or pairing responses that are received, by the transceiver(s) 916), from the external device(s) 918. In various cases, the pairer 928 causes the processor(s) 914 to initiate pairing and/or unpairing with the external device(s) 918. For example, the pairer 928 causes the processor(s) 914 to generate and/or encrypt data that the transceiver(s) 916 transmit over one or more communication channels.

EXAMPLE CLAUSES

1. A monitor-defibrillator, including: a detection circuit configured to detect an electrocardiogram (ECG) of a subject; an analog to digital converter (ADC) configured to convert the ECG to unfiltered data; an input device configured to receive an input signal from a user; a discharge circuit configured to output an electrical shock to the subject in response to the input device receiving the input signal; a transceiver configured to receive a signal from a mechanical chest compression device administering chest compressions to the subject, the signal indicating a frequency of the chest compressions; a display; and a processor configured to: generate first filtered data by removing a chest compression artifact from the unfiltered data using a first filter; determine a first shock index by analyzing the first filtered data; generate a second filter including a comb filter rejecting the frequency and harmonics of the frequency, the second filter being different than the first filter; generate second filtered data by applying the second filter to the unfiltered data; determine that the first shock index is greater than a first threshold and lower than a second threshold; in response to determining that the first shock index is greater than the first threshold and lower than the second threshold, cause the display to visually present the second filtered data; and upon expiration of a time period after outputting the second filtered data: determine a second shock index by analyzing the first filtered data; determine that the second shock index is less than the first threshold or greater than the second threshold; and in response to determining that the second shock index is less than the first threshold or greater than the second threshold, cause the display to output a recommendation to initiate the electrical shock using the input signal.

2. The monitor-defibrillator of clause 1, wherein the processor is further configured to: in response to determining that the first shock index is greater than the first threshold and lower than the second threshold, output an alert with the second filtered data.

3. The monitor-defibrillator of clause 1 or 2, wherein the first filter includes an adaptive filter, an inverse comb filter, a high-pass filter, a band reject filter, a finite impulse response (FIR) filter, or an infinite impulse response (IIR) filter.

4. A medical device, including: a sensor configured to detect a physiological parameter of a subject; a display; and a processor configured to: generate first filtered data by applying a first filter to physiological parameter data representing the physiological parameter; generate second filtered data by applying a second filter to the physiological parameter data; determine a first index by analyzing the first filtered data; determine that the first index is greater than a first threshold and lower than a second threshold; in response to determining that the first index is greater than the first threshold and lower than the second threshold, cause the display to visually present the second filtered data; and upon expiration of a time period after outputting the second filtered data: determine a second index by analyzing the first filtered data; generate a first treatment recommendation by analyzing the second index; and cause the display to visually present the first treatment recommendation.

5. The medical device of clause 4, wherein the physiological parameter includes an ECG, a transthoracic impedance, a blood pressure, a cerebral regional tissue oxygen saturation, an end-tidal CO2 (EtCO2), or a cardiopulmonary resuscitation (CPR) position.

6. The medical device of clause 4 or 5, wherein the processor is further configured to: in response to determining that the first index is greater than the first threshold and lower than the second threshold, cause the display to visually present an alert.

7. The medical device of any one of clauses 4 to 6, further including: a speaker configured to audibly output an alert, wherein the processor is further configured to: in response to determining that the first index is greater than the first threshold and lower than the second threshold, cause the speaker to output the alert.

8. The medical device of any one of clauses 4 to 7, wherein the processor is further configured to cause the display to visually present an option to initiate generation of the second index before expiration of a predetermined time after outputting the second filtered data.

9. The medical device of any one of clauses 4 to 8, wherein the first filter includes an adaptive filter, an inverse comb filter, a high-pass filter, a band reject filter, a FIR filter, or an IIR filter.

10. The medical device of any one of clauses 4 to 9, wherein the subject is receiving chest compressions from a mechanical chest compression device and the second filter includes a comb filter.

11. The medical device of any one of clauses 4 to 10, further including: a discharge circuit configured to output an electrical shock to the subject; and an input device; wherein the processor is further configured to: determine the second index is greater than the first threshold and lower than the second threshold; in response to determining that the second index is greater than the first threshold and lower than the second threshold, cause the display to visually present the second filtered data; determine that the input device has received an input signal indicating a request to administer the electrical shock to the subject; and causing the discharge circuit to output an electrical shock to the subject.

12. The medical device of any one of clauses 4 to 11, further including: a transceiver configured to communicate a signal to a mechanical chest compression device administering chest compressions to the subject; wherein the processor is further configured to: determine the second index is greater than the first threshold and lower than the second threshold; in response to determining that the second index is greater than the first threshold and lower than the second threshold, output an instruction to the mechanical chest compression device to pause chest compressions; in response to outputting the instruction to the mechanical chest compression device to pause chest compressions, determine a third index by analyzing the physiological parameter data; generate a second treatment recommendation by analyzing the third index; and cause the display to visually present the second treatment recommendation.

13. A method including: generating first filtered data by applying a first filter to physiological parameter data representing a physiological parameter; generating second filtered data by applying a second filter to the physiological parameter data; determining a first index by analyzing the first filtered data; determining that the first index is greater than a first threshold and lower than a second threshold; in response to determining that the first index is greater than the first threshold and lower than the second threshold, displaying the second filtered data; and upon expiration of a time period after outputting the second filtered data: determining a second index by analyzing the first filtered data; generating a first treatment recommendation by analyzing the second index; and displaying the first treatment recommendation on a display.

14. The method of clause 13, wherein physiological parameter includes an ECG, a transthoracic impedance, a blood pressure, a cerebral regional tissue oxygen saturation, or an EtCO2.

15. The method of clause 13 or 14, further including outputting an alert upon outputting the second filtered data.

16. The method of clause 15, wherein outputting the alert includes outputting a visual alert or outputting an aural alert.

17. The method of any one of clauses 13 to 16, wherein the first filter includes an adaptive filter, an inverse comb filter, a high-pass filter, a band reject filter, a FIR filter, or an IIR filter.

18. The method of any one of clauses 13 to 17, wherein the second filter includes a comb filter.

19. The method of any one of clauses 13 to 18, further including: determining the second index is greater than the first threshold and lower than the second threshold; in response to determining that the second index is greater than the first threshold and lower than the second threshold, causing the display to visually present the second filtered data; determining that an input device has received an input signal indicating a request to administer an electrical shock to a subject; and causing a discharge circuit to output an electrical shock to the subject.

20. The method of any one of clauses 13 to 19, further including: determining the second index is greater than the first threshold and lower than the second threshold; in response to determining that the second index is greater than the first threshold and lower than the second threshold, sending a signal to a mechanical chest compression device to pause chest compressions; while chest compressions are paused, determining a third index by analyzing the first filtered data; generating a second treatment recommendation by analyzing the third index; and causing the display to visually present the second treatment recommendation.

21. A monitor-defibrillator, including: a detection circuit configured to detect an ECG of a subject; a discharge circuit configured to output an electrical shock to the subject; an input device; a display; and a processor configured to: determine that first data indicating the ECG of the subject during a pre-charge time period is indicative of ventricular fibrillation (VF) or ventricular tachycardia (VT); in response to determining that the first data is indicative of VF or VT, cause the display to output a recommendation to administer the electrical shock to the subject; in response to causing the display to output the recommendation, determine that the input device has received an input signal indicating a request to administer the electrical shock to the subject; in response to determining that the input device has received the input signal, cause the discharge circuit to charge during a CPR period, the subject receiving chest compressions during the CPR period; determine that second data indicating the ECG of the subject during the CPR period is indicative of QRS complexes; and in response to determining that the second data is indicative of QRS complexes, cause the discharge circuit to refrain from outputting the electrical shock to the subject.

22. The monitor-defibrillator of clause 21, wherein the processor is configured to determine that the first data is indicative of VF or VT by: determining a shock index by analyzing the first data; and determining that the shock index is above an upper threshold or below a lower threshold.

23. The monitor-defibrillator of clause 22, the shock index being a first shock index, wherein the processor is configured to determine that the second data is indicative of QRS complexes by: determining a second shock index by analyzing the second data; and determining that the second shock index is below the lower threshold or above the upper threshold.

24. A medical device, including: a detection circuit configured to detect a physiological parameter of a subject; a treatment component configured to output a treatment to the subject; an input device; a display; and a processor configured to: determine an index by analyzing first data indicating the physiological parameter of the subject during a first time period; determine that the index is below a first threshold or above a second threshold; in response to determining that the index is below the first threshold or above the second threshold, cause the display to output a recommendation to administer the treatment to the subject; in response to causing the display to output the recommendation, determine that the input device has received an input signal indicating a request to administer the treatment to the subject; in response to determining that the input device has received the input signal, cause the treatment component to prepare the treatment during a second time period; determine that second data indicating the physiological parameter of the subject during the second time period is indicative of a non-pathologic condition; and in response to determining that the second data is indicative of the non-pathologic condition, cause the treatment component to refrain from outputting the treatment to the subject.

25. The medical device of clause 24, wherein the processor is configured to determine that the index is below the first threshold or above the second threshold by determining that the physiological parameter is indicative of VF or VT.

26. The medical device of clause 24 or 25, the index being a first index, wherein the processor is configured to determine that the second data is indicative of the non-pathologic condition by: determining a second index by analyzing the second data; and determining that the second index is below the first threshold or above the second threshold.

27. The medical device of any one of clauses 24 to 26, wherein the subject is receiving chest compressions during the second time period.

28. The medical device of any one of clauses 24 to 27, wherein the processor is further configured to cause the display to present an alert upon determining that the second data is indicative of the non-pathologic condition.

29. The medical device of any one of clauses 24 to 28, further including: a speaker configured to audibly present an alert, wherein the processor is further configured to cause the speaker to output the alert upon determining that the second data is indicative of the non-pathologic condition.

30. The medical device of any one of clauses 24 to 29, wherein the processor is further configured to: in response to causing the treatment component to refrain from outputting the treatment to the subject, cause the display to output a selectable option to discharge a voltage stored in the treatment component.

31. The medical device of any one of clauses 24 to 30, the index being a first index, the recommendation being a first recommendation, the input signal being a first input signal, wherein the processor is further configured to: in response to causing the treatment component to refrain from outputting the treatment to the subject, determine a second index by analyzing third data indicating the physiological parameter of the subject; determine that the second index is below the first threshold or above the second threshold; in response to determining that the second index is below the first threshold or above the second threshold, cause the display to output a second recommendation to administer the treatment to the subject; in response to causing the display to output the second recommendation, determine that the input device has received a second input signal indicating a request to administer the treatment to the subject; in response to determining that the input device has received the second input signal, cause the treatment component to charge during a fourth time period, wherein the subject is receiving chest compressions during the fourth time period; determine a third index by analyzing the physiological parameter of the subject during the fourth time period; determine that the third index is below the first threshold or above the second threshold; and in response to determining that the third index is below the first threshold or above the second threshold, cause the treatment component to output the treatment to the subject.

32. The medical device of any one of clauses 24 to 31, wherein the physiological parameter includes an (ECG, a transthoracic impedance, an airway parameter, a blood oxygenation, or a blood pressure; and wherein the treatment includes an electrical shock, chest compressions, or ventilation.

33. A method performed by a medical device including a treatment component configured to output a treatment to a subject, the method including: determining an index by analyzing first data indicating a physiological parameter of the subject during a first time period; determining that the index is below a first threshold or above a second threshold; in response to determining that the index is below a first threshold or above a second threshold, displaying a recommendation to administer the treatment to the subject; in response to displaying the recommendation, determining that an input device has received an input signal indicating a request to administer the treatment to the subject; in response to determining that the input device has received the input signal, causing the treatment component to prepare the treatment during a second time period; determining that second data indicating the physiological parameter of the subject during the second time period is indicative of a non-pathologic condition; and in response to determining that the second data is indicative of the non-pathologic condition, causing the treatment component to refrain from outputting the treatment to the subject.

34. The method of clause 33, wherein determining that the index is below the first threshold or above the second threshold includes determining that the physiological parameter is indicative of VF or VT.

35. The method of clause 33 or 34, the index being a first index, the method further including: determining that the second data is indicative of the non-pathologic condition by: determining a second index by analyzing the second data; and determining that the second index is below the first threshold or above the second threshold.

36. The method of any one of clauses 33 to 35, wherein the subject is receiving chest compressions during the second time period.

37. The method of any one of clauses 33 to 36, further including: outputting an alert upon determining that the second data is indicative of the non-pathologic condition, wherein the alert is a visual alert or an audible alert.

38. The method of any one of clauses 33 to 37, further including: in response to causing the treatment component to refrain from outputting the treatment to the subject, displaying a selectable option to discharge a voltage stored in the treatment component.

39. The method of any one of clauses 33 to 38, the index being a first index, the recommendation being a first recommendation, the input signal being a first input signal, the method further including: in response to causing the treatment component to refrain from outputting the treatment to the subject, determining a second index by analyzing third data indicating the physiological parameter of the subject; determining that the second index is below the first threshold or above the second threshold; in response to determining that the second index is below the first threshold or above the second threshold, displaying a second recommendation to administer the treatment to the subject; in response to displaying the second recommendation, determining that the input device has received a second input signal indicating a request to administer the treatment to the subject; in response to determining that the input device has received the second input signal, causing the treatment component to charge during a fourth time period, wherein the subject is receiving chest compression during the fourth time period; determining a third index by analyzing the physiological parameter of the subject during the fourth time period; determine that the third index is below the first threshold or above the second threshold; and in response to determining the third index is below the first threshold or above the second threshold, causing the treatment component to output the treatment to the subject.

40. The method of any one of clauses 33 to 39, wherein the physiological parameter includes an ECG, a transthoracic impedance, an airway parameter, a blood oxygenation, or a blood pressure; and wherein the treatment includes an electrical shock, chest compressions, or ventilation.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventors expect skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. A monitor-defibrillator, comprising:
a detection circuit configured to detect an ECG of a subject;
a discharge circuit configured to output an electrical shock to the subject;
an input device;
a display; and
a processor configured to:
determine that first data indicating the ECG of the subject during a pre-charge time period is indicative of ventricular fibrillation (VF) or ventricular tachycardia (VT);
in response to determining that the first data is indicative of VF or VT, cause the display to output a recommendation to administer the electrical shock to the subject;
in response to causing the display to output the recommendation, determine that the input device has received an input signal indicating a request to administer the electrical shock to the subject;
in response to determining that the input device has received the input signal, cause the discharge circuit to charge during a CPR period, the subject receiving chest compressions during the CPR period;
determine that second data indicating the ECG of the subject during the CPR period is indicative of QRS complexes; and
in response to determining that the second data is indicative of QRS complexes, cause the discharge circuit to refrain from outputting the electrical shock to the subject.

2. The monitor-defibrillator of claim 1, wherein the processor is configured to determine that the first data is indicative of VF or VT by:
determining a shock index by analyzing the first data; and
determining that the shock index is above an upper threshold or below a lower threshold.

3. The monitor-defibrillator of claim 2, the shock index being a first shock index, wherein the processor is configured to determine that the second data is indicative of QRS complexes by:
determining a second shock index by analyzing the second data; and
determining that the second shock index is below the lower threshold or above the upper threshold.

4. A medical device, comprising:
a detection circuit configured to detect a physiological parameter of a subject;
a treatment component configured to output a treatment to the subject;
an input device;
a display; and
a processor configured to:
determine an index by analyzing first data indicating the physiological parameter of the subject during a first time period;
determine that the index is below a first threshold or above a second threshold;
in response to determining that the index is below the first threshold or above the second threshold, cause the display to output a recommendation to administer the treatment to the subject;
in response to causing the display to output the recommendation, determine that the input device has received an input signal indicating a request to administer the treatment to the subject;

in response to determining that the input device has received the input signal, cause the treatment component to prepare the treatment during a second time period;

determine that second data indicating the physiological parameter of the subject during the second time period is indicative of a non-pathologic condition; and in response to determining that the second data is indicative of the non-pathologic condition, cause the treatment component to refrain from outputting the treatment to the subject.

5. The medical device of claim 4, wherein the processor is configured to determine that the index is below the first threshold or above the second threshold by determining that the physiological parameter is indicative of VF or VT.

6. The medical device of claim 4, the index being a first index, wherein the processor is configured to determine that the second data is indicative of the non-pathologic condition by:

determining a second index by analyzing the second data; and determining that the second index is below the first threshold or above the second threshold.

7. The medical device of claim 4, wherein the subject is receiving chest compressions during the second time period.

8. The medical device of claim 4, wherein the processor is further configured to cause the display to present an alert upon determining that the second data is indicative of the non-pathologic condition.

9. The medical device of claim 4, further comprising:

a speaker configured to audibly present an alert, wherein the processor is further configured to cause the speaker to output the alert upon determining that the second data is indicative of the non-pathologic condition.

10. The medical device of claim 4, wherein the processor is further configured to:

in response to causing the treatment component to refrain from outputting the treatment to the subject, cause the display to output a selectable option to discharge a voltage stored in the treatment component.

11. The medical device of claim 4, the index being a first index, the recommendation being a first recommendation, the input signal being a first input signal, wherein the processor is further configured to:

in response to causing the treatment component to refrain from outputting the treatment to the subject, determine a second index by analyzing third data indicating the physiological parameter of the subject;

determine that the second index is below the first threshold or above the second threshold;

in response to determining that the second index is below the first threshold or above the second threshold, cause the display to output a second recommendation to administer the treatment to the subject;

in response to causing the display to output the second recommendation, determine that the input device has received a second input signal indicating a request to administer the treatment to the subject;

in response to determining that the input device has received the second input signal, cause the treatment component to charge during a fourth time period, wherein the subject is receiving chest compressions during the fourth time period;

determine a third index by analyzing the physiological parameter of the subject during the fourth time period;

determine that the third index is below the first threshold or above the second threshold; and in response to determining that the third index is below the first threshold or above the second threshold, cause the treatment component to output the treatment to the subject.

12. The medical device of claim 4, wherein the physiological parameter comprises an ECG, a transthoracic impedance, an airway parameter, a blood oxygenation, or a blood pressure; and wherein the treatment comprises an electrical shock, chest compressions, or ventilation.

13. A method performed by a medical device comprising a treatment component configured to output a treatment to a subject, the method comprising:

determining an index by analyzing first data indicating a physiological parameter of the subject during a first time period;

determining that the index is below a first threshold or above a second threshold;

in response to determining that the index is below a first threshold or above a second threshold, displaying a recommendation to administer the treatment to the subject;

in response to displaying the recommendation, determining that an input device has received an input signal indicating a request to administer the treatment to the subject;

in response to determining that the input device has received the input signal, causing the treatment component to prepare the treatment during a second time period;

determining that second data indicating the physiological parameter of the subject during the second time period is indicative of a non-pathologic condition; and in response to determining that the second data is indicative of the non-pathologic condition, causing the treatment component to refrain from outputting the treatment to the subject.

14. The method of claim 13, wherein determining that the index is below the first threshold or above the second threshold comprises determining that the physiological parameter is indicative of VF or VT.

15. The method of claim 13, the index being a first index, the method further comprising:

determining that the second data is indicative of the non-pathologic condition by:

determining a second index by analyzing the second data; and determining that the second index is below the first threshold or above the second threshold.

16. The method of claim 13, wherein the subject is receiving chest compressions during the second time period.

17. The method of claim 13, further comprising:

outputting an alert upon determining that the second data is indicative of the non-pathologic condition, wherein the alert is a visual alert or an audible alert.

18. The method of claim 13, further comprising:

in response to causing the treatment component to refrain from outputting the treatment to the subject, displaying a selectable option to discharge a voltage stored in the treatment component.

19. The method of claim 13, the index being a first index, the recommendation being a first recommendation, the input signal being a first input signal, the method further comprising:

in response to causing the treatment component to refrain from outputting the treatment to the subject, determining a second index by analyzing third data indicating the physiological parameter of the subject;

determining that the second index is below the first threshold or above the second threshold;

in response to determining that the second index is below the first threshold or above the second threshold, displaying a second recommendation to administer the treatment to the subject;

in response to displaying the second recommendation, determining that the input device has received a second input signal indicating a request to administer the treatment to the subject;

in response to determining that the input device has received the second input signal, causing the treatment component to charge during a fourth time period, wherein the subject is receiving chest compression during the fourth time period;

determining a third index by analyzing the physiological parameter of the subject during the fourth time period;

determine that the third index is below the first threshold or above the second threshold; and in response to determining the third index is below the first threshold or above the second threshold, causing the treatment component to output the treatment to the subject.

20. The method of claim 13, wherein the physiological parameter comprises an ECG, a transthoracic impedance, an airway parameter, a blood oxygenation, or a blood pressure; and wherein the treatment comprises an electrical shock, chest compressions, or ventilation.

* * * * *